United States Patent
Inukai et al.

(10) Patent No.: US 10,208,034 B2
(45) Date of Patent: Feb. 19, 2019

(54) QUINOLINE DERIVATIVE

(71) Applicant: ONO PHARMACEUTICAL CO., LTD., Osaka (JP)

(72) Inventors: Takayuki Inukai, Osaka (JP); Jun Takeuchi, Osaka (JP); Tomoko Yasuhiro, Osaka (JP)

(73) Assignee: ONO PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 15/539,530

(22) PCT Filed: Dec. 24, 2015

(86) PCT No.: PCT/JP2015/086050
§ 371 (c)(1),
(2) Date: Jun. 23, 2017

(87) PCT Pub. No.: WO2016/104617
PCT Pub. Date: Jun. 30, 2016

(65) Prior Publication Data
US 2017/0349583 A1 Dec. 7, 2017

(30) Foreign Application Priority Data
Dec. 25, 2014 (JP) .................... 2014-262146

(51) Int. Cl.
*A61K 31/517* (2006.01)
*C07D 471/04* (2006.01)
*C07D 401/14* (2006.01)
*A61K 31/4709* (2006.01)
*A61K 31/55* (2006.01)

(52) U.S. Cl.
CPC ........ *C07D 471/04* (2013.01); *A61K 31/4709* (2013.01); *A61K 31/517* (2013.01); *A61K 31/55* (2013.01); *C07D 401/14* (2013.01)

(58) Field of Classification Search
CPC ... C07D 401/14; C07D 471/00; C07D 471/04
See application file for complete search history.

(56) References Cited

U.S. PATENT DOCUMENTS

| | | | |
|---|---|---|---|
| 9,562,060 B2* | 2/2017 | Cheng ................. | C07D 471/04 |
| 9,573,935 B2* | 2/2017 | Inukai ................. | C07D 401/14 |
| 2007/0060613 A1 | 3/2007 | Kim | |
| 2008/0312232 A1 | 12/2008 | Kim et al. | |
| 2009/0274693 A1 | 11/2009 | Gilmer et al. | |
| 2009/0306103 A1 | 12/2009 | Boyer et al. | |
| 2011/0053931 A1 | 3/2011 | Gaudino et al. | |
| 2011/0092503 A1 | 4/2011 | Ullrich et al. | |
| 2011/0118252 A1 | 5/2011 | Kim et al. | |
| 2012/0070413 A1 | 3/2012 | Kim et al. | |
| 2013/0142790 A1 | 6/2013 | Gilmer et al. | |
| 2013/0150363 A1 | 6/2013 | Gilmer et al. | |
| 2014/0018365 A1 | 1/2014 | Schultz-Fademrecht et al. | |
| 2014/0206679 A1* | 7/2014 | Cheng ................. | C07D 471/04 514/230.5 |
| 2014/0275077 A1 | 9/2014 | Dandu et al. | |
| 2016/0168121 A1 | 6/2016 | Inukai et al. | |
| 2017/0088542 A1* | 3/2017 | Inukai ................. | C07D 401/14 |

FOREIGN PATENT DOCUMENTS

| | | |
|---|---|---|
| CN | 101528702 A | 9/2009 |
| CN | 102083824 A | 6/2011 |
| CN | 103124729 A | 5/2013 |
| JP | 2008-539275 A | 11/2008 |
| JP | 2009-537632 A | 10/2009 |
| JP | 2009-539878 A | 11/2009 |
| JP | 2010-178651 A | 8/2010 |
| JP | 2011-517689 A | 6/2011 |
| JP | 2014-533287 A | 12/2014 |
| WO | 2006/116713 A1 | 11/2006 |
| WO | WO-2006116713 A1 * | 11/2006 ........... C07D 401/12 |

(Continued)

OTHER PUBLICATIONS

X. Wu et al., 5 Oncotarget, 9546-9563 (2014).*
T. Fujimori et al., 8 Mucosal Immunology 1021-1030 (2015).*
R. Linger et al., Advances in Cancer Research, 35-83 (2008).*
C.V. Rothin et al., 22 Current Opinion in Immunology, 740-746 (2010).*
A. Zagórska et al. 15, Nature Immunology, 920-928 (2014).*
C.V. Rothin et al., 33 Annual Reviews of Immunology, 355-391 (2015).*
A. Fiebeler et al., 43 American Journal of Kidney Diseases, 286-295 (2004).*
Z. Wang et al., 19 Drug Discovery Today, 145-150 (2014).*
U.K. Marelli et al., 3 Frontiers in Oncology, 1-12 (2013).*

(Continued)

*Primary Examiner* — Alexander R Pagano
(74) *Attorney, Agent, or Firm* — Sughrue Mion, PLLC

(57) ABSTRACT

A compound represented by general formula (I) and having a quinoline skeleton has a strong Axl inhibitory activity, and therefore the compound can be an agent for treating Axl-related diseases, for example, cancer such as acute myeloid leukemia, chronic myeloid leukemia, melanoma, breast cancer, pancreatic cancer, and glioma, kidney diseases, immune system diseases, and circulatory system diseases.

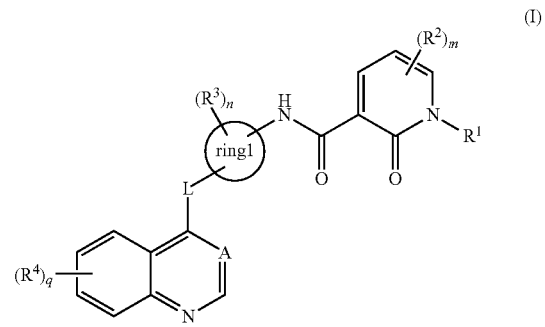

11 Claims, No Drawings

(56) References Cited

FOREIGN PATENT DOCUMENTS

| WO | 2007/033196 | A1 | | 3/2007 | |
|---|---|---|---|---|---|
| WO | 2007/146824 | A2 | | 12/2007 | |
| WO | 2008/048375 | A1 | | 4/2008 | |
| WO | 2009/137429 | A1 | | 11/2009 | |
| WO | 2009/140549 | A1 | | 11/2009 | |
| WO | 2010/039248 | A1 | | 4/2010 | |
| WO | 2012/011548 | A1 | | 1/2012 | |
| WO | 2012/028332 | A1 | | 3/2012 | |
| WO | 2012/080729 | A2 | | 6/2012 | |
| WO | 2013/074633 | A1 | | 5/2013 | |
| WO | 2015/012298 | A1 | | 1/2015 | |
| WO | WO-2015012298 | A1 | * | 1/2015 | ........... C07D 401/14 |

OTHER PUBLICATIONS

B. VandenBrink et al., 39 The American Society for Pharmacology and Experimental Therapeutics, 1546-1554 (2011).*
Extended European Search Report dated Nov. 15, 2017, issued by the European Patent Office in counterpart European Application No. 15873185.1.
Samit K Bhattacharya et al: "Identification of novel series of pyrazole and indole-urea based DFG-out PYK2 inhibitors", Bioorganic & Medicinal Chemistry Letters, vol. 22, No. 24, Dec. 1, 2012, XP05509390, pp. 7523-7529, (7 pages total).
Allen G et al: "Identification of small molecule inhibitors of proline-rich tyrosine kinase 2 (Pyk2) with osteogenic activity in osteoblast cells", Bioorganic & Medicinal Chemistry Letters, vol. 19, No. 17, Sep. 1, 2009, XP026458526, pp. 4924-4928, (5 pages total).
Search Report dated Feb. 9, 2016, issued by the International Searching Authority in counterpart International Application No. PCT/JP2015/086050 (PCT/ISA/210).
Written Opinion dated Feb. 9, 2016, issued by the International Searching Authority in counterpart International Application No. PCT/JP2015/086050 (PCT/ISA/237).
Zhang, et al.; "Discovery of novel type II c-Met inhibitors based on BMS-777607", European Journal of Medicinal Chemistry, vol. 80, Apr. 2014, 13 pages total.
Lovering, et al.; "Identification of Type-II Inhibitors Using Kinase Structures", Chemical Biology and Drug Design, vol. 80, No. 5, Jun. 2012, 8 pages total.
Korshunov, "Axl-dependent signalling: a clinical update", Clinical Science, vol. 122, 2012, 8 pages total.
Gjerdrum, et al.; "Axl is an essential epithelial-to-mesenchymal transition-induced regulator of breast cancer metastasis and patient survival", Proceedings of the National Academy of Sciences, vol. 107, No. 3, Jan. 2010, 6 pages total.
Park, et al.; "Inhibition of the receptor tyrosine kinase Axl impedes activation of the FLT3 internal tandem duplication in human acute myeloid leukemia: implications for Axl as a potential therapeutic target", Blood, vol. 121, No. 11, Mar. 2013, 11 pages total.
Communication dated Dec. 6, 2016, issued by the European Patent Office in related European Application No. 14828976.2.
Registry (STN) [online], Jan. 16, 2001, RN 314026-41-0, [retrieval date Aug. 6, 2014], 1 page total.
Communication dated Nov. 2, 2016, issued by the State Intellectual Property Office of the People's Republic of China in counterpart Chinese Application No. 201480041780.2.
Search Report dated Aug. 19, 2014, issued by the International Searching Authority in related International Application No. PCT/JP2014/069419 (PCT/ISA/210).
Written Opinion dated Aug. 19, 2014, issued by the International Searching Authority in related International Application No. PCT/JP2014/069419 (PCT/ISA/237).
Related U.S. Appl. No. 15/373,091, filed Dec. 8, 2016.

* cited by examiner

QUINOLINE DERIVATIVE

TECHNICAL FIELD

The present invention relates to a compound represented by general formula (I):

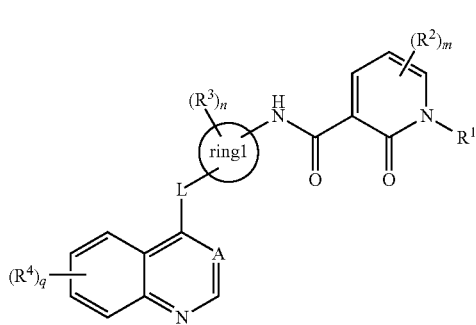

(I)

(wherein all of the symbols have the same meanings as given below), a salt thereof, a solvate thereof, an N-oxide thereof, or a prodrug of these (hereinafter, also abbreviated as the compound of the present invention).

BACKGROUND ART

Axl (also known as: UFO, ARK, Tyro7) is a receptor tyrosine kinase belonging to a TAM family (Axl, Mer and Tyro3) cloned from tumor cells. Gas6 (growth-arrest-specific protein 6) cloned as a gene specifically expressed at the time of cell proliferation arrest is known as a ligand for Axl. Axl activated by binding of Gas6 transfers a signal via phosphorylation. Since the signal activates an Erk1/2 pathway or a PI3K/Akt pathway, the activation of Axl is known to be involved in pathologic conditions of cancers, immune system diseases, circulatory system diseases, and the like (see, Non-Patent Literature 1).

In particular, the relation between Axl and various types of cancers is well known. For example, it is known that the expression of Axl is involved in metastasis and prognosis of breast cancer (see, Non-Patent Literature 2), and that Axl is involved in the pathologic conditions of acute myeloid leukemia (AML) (see Non-Patent Literature 3). Therefore, it is considered that compounds which inhibit the activation of Axl are useful for treatment of various types of cancers, immune system diseases, and circulatory system diseases.

By the way, as prior art of the compound of the present invention, a compound represented by general formula (A):

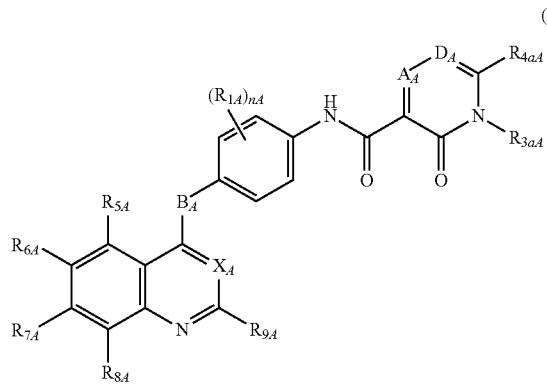

(A)

(wherein $X_A$ represents —$CR_{12A}$ or N; $B_A$ represents O, S, —SO, and the like; $A_A$ represents —$CR_{dA}$ or N; $D_A$ represents —$CR_{eA}$ or N; each $R_{1A}$ independently represents a hydrogen atom, halogen, cyano, and the like; $R_{3aA}$ represents a hydrogen atom, alkyl, aryl, and the like; $R_{6A}$ and $R_{7A}$ independently represent a hydrogen atom, halogen, —$OR_{13A}$, and the like; and $R_{13A}$ represents a hydrogen atom, alkyl, and the like (where the definitions of the groups are excerpted) is known to be a c-Met inhibitor (see, Patent Literature 1).

Furthermore, a compound represented by general formula (B):

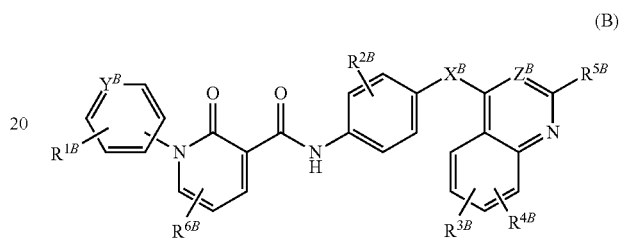

(B)

(wherein $X^B$ represents an oxygen atom or a sulfur atom; $Y^B$ and $Z^B$ independently CH or N; $R^{1B}$ represents a hydrogen atom, a halogen atom, cyano, and the like; $R^{2B}$ represents a hydrogen atom, a halogen atom, and the like; $R^{3B}$ and $R^{4B}$ independently represent a hydrogen atom, a halogen atom, $OR^{11B}$, and the like, $R^{5B}$ represents a hydrogen atom, $OR^{11B}$, and the like; $R^{6B}$ represents a linear, branched or cyclic C1-6 alkyl group optionally substituted with a hydrogen atom, a halogen atom, and the like, $R^{11B}$ represents a linear, branched or cyclic C1-6 alkyl group, and the like (where the definitions of the groups are excerpted)) is known to be a c-Met inhibitor (see, Patent Literature 2).

On the other hand, a compound having a quinoline skeleton and represented by formula (C):

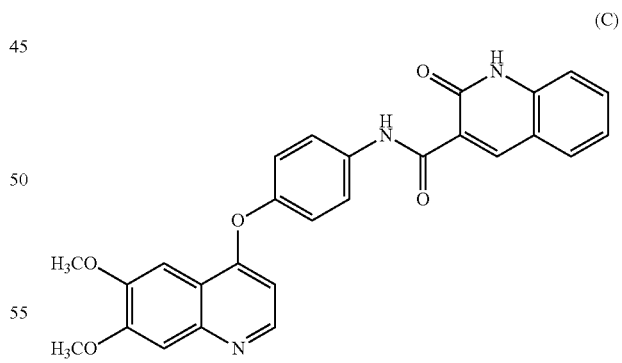

(C)

is known to have an ASK1 inhibitory activity and be an agent for preventing and/or treating amyotrophic lateral sclerosis (ALS) (see Patent Literature 3).

Furthermore, a compound represented by general formula (D):

$$R^D-X^D-W^D-Y^D-R^{1D}$$ (D)

(wherein $R^D$ represents

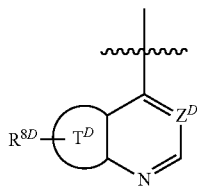

or the like; $T^D$ represents phenyl or the like; $Z^D$ represents N or $CR^{7D}$; $W^D$ represents a substituted or unsubstituted phenyl, substituted or unsubstituted 6-membered nitrogen-containing heteroaryl or the like; $X^D$ represents O, S, S(=O), or the like; $Y^D$ represents $NR^{aD}$ C(=O)—$(CR^{3D}R^{4D})_p$— or the like; $R^{aD}$ represents, a hydrogen atom, an alkyl group, or the like; and $R^{1D}$ represents

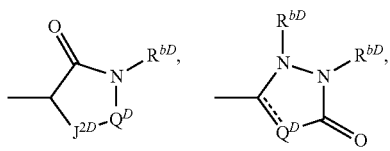

or the like; $J^{2D}$ represents O or $CR^{4aD}R^{4aD}$; $Q^D$ represents 1- to 5-membered saturated or partially unsaturated alkyl chain or the like; $R^{1D}$ represents optionally substituted phenyl or may be fused to optionally substituted 5- to 6-membered heterocycle; $R^{3D}$ and $R^{4D}$ each independently represents a hydrogen atom, an alkyl group, an aryl group, or the like; $R^{4aD}$ is absent or represents a hydrogen atom, a halogen atom, or the like (where the definitions of the groups are excerpted)) is known to be a c-Met inhibitor (see Patent Literature 4).

Furthermore, a compound represented by general formula (E):

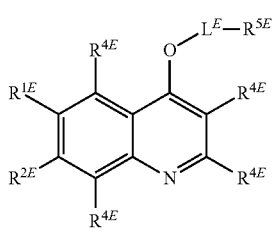

(wherein $R^{1E}R^{2E}$ and $R^{4E}$ independently represent H, F, Cl, Br, I, CN, $OR^{10E}$, C1-C12 alkyl, or the like; $L^E$ represents a C3-C12 carbon ring, C6-C20 aryl, or the like; $R^{5E}$ represents —C(=$Y^E$)$R^{13E}$; —C(=$Y^E$)$R^{10E}R^{13E}$; —$NR^{10E}C$(=$Y^E$)$R^{13E}$; or the like; $R^{10E}$ represents H, C1-C12 alkyl, a C3-C12 carbon ring, a C2-C20 heterocycle, or the like; $R^{13E}$ represents H, C1-C6 alkyl, or the like; and $Y^E$ represents O or S (where the definitions of the groups are excerpted)) is known to be a c-Met inhibitor (see Patent Literature 5).

Any of the prior art literatures neither mention nor suggest that the compound represented by the general formula (I) of the present invention has an Axl inhibitory activity.

PRIOR ART LITERATURES

[Patent Literature 1] WO2007/033196
[Patent Literature 2] WO2008/048375
[Patent Literature 3] WO2012/011548
[Patent Literature 4] WO2006/116713
[Patent Literature 5] WO2007/146824

Non-Patent Literatures

[Non-Patent Literature 1] Clinical Science, Vol. 122, pp. 361-368, 2012
[Non-Patent Literature 2] Proceedings of the national academy of sciences of the United States of America, Vol. 107, No. 3, pp. 1124-1129, 2010
[Non-Patent Literature 3] Blood, Vol. 121, pp. 2064-2073, 2013

SUMMARY OF INVENTION

Technical Problem

A problem to be solved by the present invention is to find a compound having an Axl inhibitory activity, which is useful for treatment of cancer such as AML, and to provide the compound as pharmaceuticals.

Solution to Problem

In order to solve the above-mentioned problem, the inventors of the present invention have keenly studied to find a compound strongly inhibiting Axl. As a result, surprisingly, the inventors have found that a compound of the present invention has strong Axl inhibitory activity, and completed the present invention.

That is to say, the present invention relates to:
[1] a compound represented by the general formula (I)

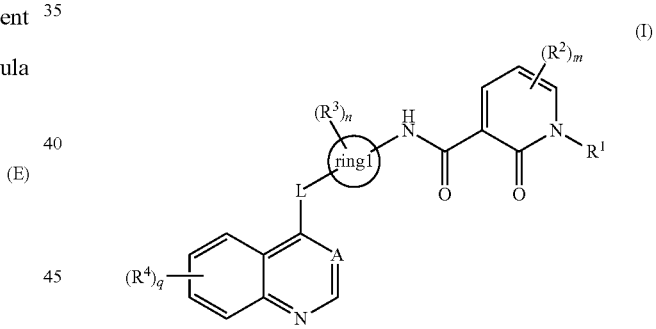

[wherein
$R^1$ represents (1) a C1-8 alkyl group optionally substituted with one to five $R^{11}$, (2) a C3-7 carbon ring optionally substituted with one to five $R^{12}$, or (3) a 4- to 7-membered heterocycle optionally substituted with one to five $R^{13}$, where when the C1-8 alkyl group represented by $R^1$ is a branched alkyl group, C1-3 alkyl groups branched from the same carbon atom may together form a saturated C3-7 carbon ring;
$R^2$ represents (1) a C1-8 alkyl group optionally substituted with one to five $R^{21}$, (2) a C2-8 alkenyl group optionally substituted with one to five $R^{22}$, (3) a C2-8 alkynyl group optionally substituted with one to five $R^{23}$, (4) a —$OR^{24}$ group, (5) a C3-7 carbon ring optionally substituted with one to five $R^{25}$, (6) a 4- to 7-membered heterocycle optionally substituted with one to five $R^{26}$, (7) a halogen atom, (8) a C(O)$R^{27}$ group, or (9) a C(O)$NR^{28}R^{29}$ group, where when m is two or more and $R^2$ is on adjacent carbon atoms and when $R^2$ represents a C1-3 alkyl group optionally substituted with an amino group, or a C2-3 alkenyl group optionally substituted with an amino group, $R^2$ bonded to the adjacent carbon atoms, together with the carbon atoms, may form a 5- to 7-membered cyclic group optionally substituted with one to three $R^{20}$, and when $R^1$ represents a C1-3 alkyl group, together with the atom on the 5- to 7-membered cyclic group formed by the plurality of $R^2$ may further form a 5- to 7-membered cyclic group;

$R^3$ represents (1) a C1-4 alkyl group, (2) a halogen atom, (3) a C1-4 haloalkyl group, or (4) —$OR^{31}$ group;

$R^4$ represents (1) a C1-4 alkoxy group, (2) a C1-4 haloalkyl group, (3) an —$OR^{41}$ group, (4) a C1-4 alkyl group, (5) a C2-4 alkenyloxy group, or (6) a C2-4 alkynyloxy group;

$R^{11}$ represents (1) an —$OR^{101}$ group, (2) an $SO_2R^{102}$ group, (3) an $NR^{103}R^{104}$ group, or (4) a C3-7 carbon ring optionally substituted with one to three halogen atoms;

$R^{12}$ represents (1) a C1-4 alkyl group optionally substituted with an amino group, (2) a C1-4 haloalkyl group, or (3) a halogen atom;

$R^{13}$ represents (1) a C1-4 alkyl group optionally substituted with an amino group, (2) a C1-4 haloalkyl group, or (3) a halogen atom;

$R^{101}$ represents (1) a hydrogen atom, or (2) a C1-4 alkyl group;

$R^{102}$ represents (1) a hydrogen atom, or (2) a C1-4 alkyl group;

$R^{103}$ and $R^{104}$ each independently represents (1) a hydrogen atom, or (2) a C1-4 alkyl group;

$R^{20}$ represents (1) a C1-4 alkyl group, (2) a halogen atom, (3) a C1-4 haloalkyl group, (4) an oxo group, (5) an —$OR^{201}$ group, (6) a $COOR^{205}$ group, (7) an $NR^{206}R^{207}$ group, or (8) a $COR^{208}$ group, where when two $R^{20}$ represent a C1-3 alkyl group and are on the same carbon atom, the $R^{20}$ together may form a C3-7 saturated carbon ring;

$R^{21}$, $R^{22}$, and $R^{23}$ each independently represents (1) a halogen atom, (2) an —$OR^{202}$ group, or (3) an $NR^{203}R^{204}$ group;

$R^{24}$ represents (1) a hydrogen atom, (2) a C1-4 alkyl group, or (3) a 4- to 10-membered heterocycle, $R^{25}$ and $R^{26}$ each independently represents (1) a C1-4 alkyl group, or (2) a halogen atom;

$R^{27}$ represents (1) a hydrogen atom, (2) a C1-4 alkyl group, or (3) a C3-7 carbon ring;

$R^{28}$ and $R^{29}$ each independently represents (1) a hydrogen atom, (2) a C1-4 alkyl group, or (3) a C3-7 carbon ring;

$R^{201}$ represents (1) a hydrogen atom, or (2) a C1-4 alkyl group;

$R^{202}$ represents (1) a hydrogen atom, or (2) a C1-4 alkyl group;

$R^{203}$ and $R^{204}$ each independently represents (1) a hydrogen atom, or (2) a C1-4 alkyl group, (3) a $C(O)R^{210}$ group, or (4) a $COOR^{217}$ group;

$R^{205}$ represents (1) a hydrogen atom, or (2) a C1-4 alkyl group;

$R^{206}$ and $R^{207}$ each independently represents (1) a hydrogen atom, or (2) a C1-4 alkyl group;

$R^{208}$ represents (1) a hydrogen atom, (2) a C1-4 alkyl group, (3) a C2-4 alkenyl group, or (4) a C2-4 alkynyl group;

$R^{210}$ represents (1) a C1-4 alkyl group optionally substituted with $NR^{211}R^{212}$ or a cyano group, (2) a C2-4 alkenyl group optionally substituted with $NR^{213}R^{214}$ or a cyano group, or (3) a C2-4 alkynyl group optionally substituted with $NR^{215}R^{216}$ or a cyano group;

$R^{211}$, $R^{212}$, $R^{213}$, $R^{214}$, $R^{215}$, $R^{216}$ and $R^{217}$ each independently represents (1) a hydrogen atom, or (2) a C1-4 alkyl group;

$R^{31}$ represents (1) a hydrogen atom, (2) a C1-4 alkyl group, or (3) a C1-4 haloalkyl group;

$R^{41}$ represents (1) a hydrogen atom; (2) a C1-8 alkyl group substituted with one to two substituents selected from the group consisting of (a) a 5- to 7-membered cyclic group optionally substituted with one to two substituents selected from the group consisting of (i) a C1-4 alkyl group, (ii) a C1-4 haloalkyl group, and (iii) a halogen atom, (b) $NR^{401}R^{402}$, (c) a hydroxyl group, and (d) an $SO_2R^{403}$ group; (3) a C2-8 alkenyl group substituted with one to two substituents selected from the group consisting of (a) a 5- to 7-membered cyclic group optionally substituted with one to two substituents selected from the group consisting of (i) a C1-4 alkyl group, (ii) a C1-4 haloalkyl group, and (iii) a halogen atom, (b) $NR^{401}R^{402}$, (c) a hydroxyl group, and (d) an $SO_2R^{403}$ group; or (4) a C2-8 alkynyl group substituted with one to two substituents selected from the group consisting of (a) a 5- to 7-membered cyclic group optionally substituted with one to two substituents selected from the group consisting of (i) a C1-4 alkyl group, (ii) a C1-4 haloalkyl group, and (iii) a halogen atom, (b) $NR^{401}R^{402}$ (c) a hydroxyl group, and (d) an $SO_2R^{403}$ group, $R^{401}$ and $R^{402}$ each independently represents (1) a hydrogen atom, or (2) a C1-4 alkyl group;

$R^{403}$ represents (1) a hydrogen atom, or (2) a C1-4 alkyl group;

A represents (1) CH, or (2) a nitrogen atom;

L represents (1) —O—, (2) —NH—, (3) —C(O)—, (4) —$CR^6R^7$—, (5) —S—, (6) —S(O)—, or (7) —$S(O)_2$—;

$R^6$ and $R^7$ each independently represents (1) a hydrogen atom, (2) a halogen atom, (3) a C1-4 alkyl group, (4) a hydroxyl group, or (5) $NH_2$;

ring1 represents a 5- to 7-membered cyclic group;

$R^{11}$, $R^{12}$, $R^{13}$, $R^{20}$, $R^{21}$, $R^{22}$, $R^{23}$, $R^{25}$, or $R^{26}$, when being a plurality of groups, may be the same as or different from each other;

m represents an integer of 0 to 3;

n represents an integer of 0 to 3;

q represents an integer of 0 to 4 when m is two or more, a plurality of $R^2$ may be the same as or different from each other;

when n is two or more, a plurality of $R^3$ may be the same as or different from each other;

when q is two or more, a plurality of $R^4$ may be the same as or different from each other;

where a ring represented by the following formula:

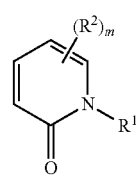

does not represent a ring represented by the following formula:

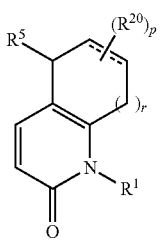

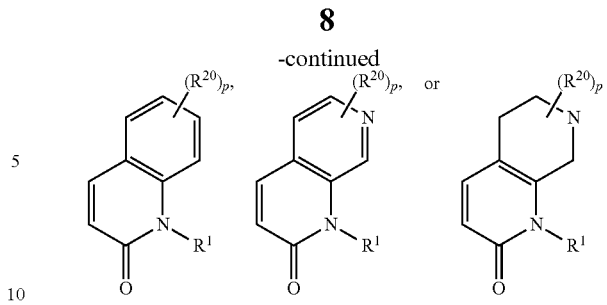

(wherein

------ represents a single bond or a double bond, $R^5$ represents (1) a hydrogen atom, (2) a C1-4 alkyl group, (3) a halogen atom, (4) a C1-4 haloalkyl group, or (5) a —$OR^{51}$ group, where $R^{51}$ represents (1) a hydrogen atom or (2) a C1-4 alkyl group, p represents an integer of 0 to 3, when p is two or more, a plurality of $R^{20}$ may be the same as or different from each other; r represents an integer of 0 to 2)], a salt thereof, a solvate thereof, an N-oxide thereof, or a prodrug of these,

[2] the compound according to the above-mentioned [1], wherein $R^2$ represents (1) a C1-8 alkyl group optionally substituted with one to five $R^{21}$, (2) a C2-8 alkenyl group optionally substituted with one to five $R^{22}$, (3) a C2-8 alkynyl group optionally substituted with one to five $R^{23}$, (4) a halogen atom, or (5) a $C(O)R^{27}$ group,

[3] the compound according to the above-mentioned [1], wherein in the general formula (I), a ring represented by the following formula:

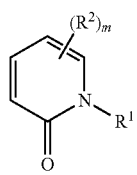

is a ring represented by the following formula:

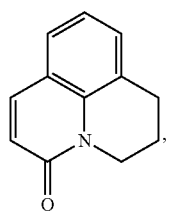 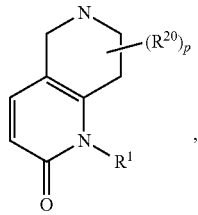

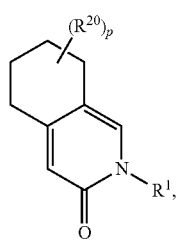 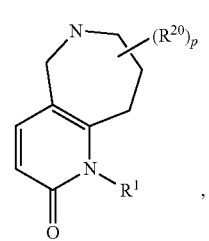

[wherein p represents an integer of 0 to 3, when p is two or more, a plurality of $R^{20}$ may be the same as or different from each other, and a nitrogen atom represents —NH— when $R^{20}$ is not substituted with the nitrogen atom, and the other symbols have the same meanings as defined in the above-mentioned [1].],

[4] the compound according to any one of the above-mentioned [1] to [3], wherein the ring1 is benzene or pyridine,

[5] the compound according to any one of the above-mentioned [1] to [4], wherein L is (1) —O—, (2) —NH—, or (3) —C(O)—,

[6] the compound according to the above-mentioned [1], wherein the compound is (1) 5-acetyl-N-{5-[(6,7-dimethoxy-4-quinolinyl)oxy]-2-pyridinyl}-6-methyl-2-oxo-1-phenyl-1,2-dihydro-3-pyridinecarboxamide, (2) N-{5-[(6,7-dimethoxy-4-quinolinyl)oxy]-2-pyridinyl}-3,8-dioxo-2-phenyl-2,3,5,6,7,8-hexahydro-4-isoquinolinecarboxamide, (3) N-{5-[(6,7-dimethoxy-4-quinolinyl)oxy]-2-pyridinyl}-2,5-dioxo-1-phenyl-2,5,6,7,8,9-hexahydro-1H-pyrido[3,2-c]azepine-3-carboxamide, (4) 7-amino-N-{5-[(6,7-dimethoxy-4-quinolinyl)oxy]-2-pyridinyl}-2-oxo-1-phenyl-1,2-dihydro-3-quinolinecarboxamide, (5) N-{5-[(6,7-dimethoxy-4-quinolinyl)oxy]-2-pyridinyl}-2-oxo-1-phenyl-1,2-dihydro-1,7-naphthyridine-3-carboxamide, or (6) 7-(2-butynoyl)-N-{5-[(6,7-dimethoxy-4-quinolinyl)oxy]-2-pyridinyl}-2-oxo-1-phenyl-1,2,5,6,7,8-hexahydro-1,7-naphthyridine-3-carboxamide,

[7] a pharmaceutical composition containing the compound represented by the general formula (I) as defined in the above-mentioned [1], a salt thereof, a solvate thereof, an N-oxide thereof, or a prodrug of these,

[8] the pharmaceutical composition according to the above-mentioned [7], which is an Axl inhibitor,

[9] the pharmaceutical composition according to the above-mentioned [7], which is an agent for preventing and/or treating an Axl-related disease,

[10] the pharmaceutical composition according to the above-mentioned [9], wherein the Axl-related diseases includes cancer, kidney diseases, immune system diseases, or circulatory system diseases,

[11] the pharmaceutical composition according to the above-mentioned [10], wherein the cancer is acute myeloid leukemia, chronic myeloid leukemia, acute lymphatic leukemia, chronic lymphatic leukemia, multiple myeloma, melanoma, breast cancer, pancreatic cancer, glioma, esophageal adenocarcinoma, large intestine cancer, renal cell carcinoma, thyroid cancer, non-small cell lung cancer, prostate cancer, stomach cancer, liver cancer, uveal malignant melanoma, ovarian cancer, endometrial cancer, lymphoma, head and neck cancer, or sarcoma,

[12] the pharmaceutical composition according to the above-mentioned [7], which is a metastasis suppressing agent for cancer cells,

[13] a method for preventing and/or treating an Axl-related disease, the method including administering an effective amount of a compound represented by the general formula (I) as defined in the above-mentioned [1], a salt thereof, a solvate thereof, an N-oxide thereof, or a prodrug of these, to a mammal,

[14] a compound represented by the general formula (I) according to the above-mentioned [1], a salt thereof, a solvate thereof, an N-oxide thereof, or a prodrug, for preventing and/or treating an Axl-related disease, and

[15] use of a compound represented by the general formula (I), a salt thereof, a solvate thereof, an N-oxide thereof, or a prodrug, as defined in the above-mentioned [1], to manufacture an agent for preventing and/or treating an Axl-related disease.

Advantageous Effects of Invention

A compound of the present invention has a strong Axl inhibitory activity, has an Axl-selective inhibitory activity to a specific kinase, and has reduced CYP inhibitory effect, and therefore is useful as a therapeutic drug for acute myeloid leukemia or the like, has less side effect and has little concern about drug interaction.

DESCRIPTION OF EMBODIMENTS

The present invention will be described in detail hereinafter.

In the present invention, a halogen atom denotes a fluorine atom, a chlorine atom, a bromine atom, and an iodine atom.

In the present invention, the C1-8 alkyl group includes a linear or branched C1-8 alkyl group. Examples thereof include methyl, ethyl, propyl, butyl, pentyl, hexyl, heptyl, octyl, isopropyl, isobutyl, sec-butyl, tert-butyl, and an isomer thereof.

In the present invention, the C1-4 alkyl group includes a linear or branched C1-4 alkyl group. Examples thereof include methyl, ethyl, propyl, butyl, isopropyl, isobutyl, sec-butyl, and tert-butyl.

In the present invention, the C1-3 alkyl group includes a linear or branched C1-3 alkyl group. Examples thereof include a methyl group, an ethyl group, a propyl group, and an isopropyl.

In the present invention, the C1-4 haloalkyl group denotes, for example, a fluoromethyl group, a chloromethyl group, a bromomethyl group, an iodomethyl group, a difluoromethyl group, a trifluoromethyl group, a 1-fluoroethyl group, a 2-fluoroethyl group, a 2-chloroethyl group, a pentafluoroethyl group, a 1-fluoropropyl group, a 2-chloropropyl group, a 3-fluoropropyl group, a 3-chloropropyl group, a 4,4,4-trifluorobutyl group, and a 4-bromobutyl group.

In the present invention, the C2-8 alkenyl group denotes, for example, a vinyl group, a propenyl group, a butenyl group, a pentenyl group, a hexenyl group, a heptenyl group, and an octenyl group, and an isomer thereof, and the like.

In the present invention, the C2-4 alkenyl group includes a linear or branched C2-4 alkenyl group, and examples thereof include ethenyl, propenyl, butenyl, and an isomer thereof, and the like.

In the present invention, the C2-3 alkenyl group includes a linear or branched C2-3 alkenyl group, and examples thereof include ethenyl, propenyl, and an isomer thereof, and the like.

In the present invention, the C2-8 alkynyl group denotes, for example, an ethynyl group, a propynyl group, a butynyl group, a pentynyl group, a hexynyl group, a heptynyl group, an octynyl group, and an isomer thereof.

In the present invention, the C2-4 alkynyl group includes a linear or branched C2-4 alkynyl group, and examples thereof include ethynyl, propynyl, butynyl, and an isomer thereof.

In the present invention, the C1-8 alkylene group includes a linear or branched C1-8 alkylene group, and examples thereof include methylene, ethylene, propylene, butylene, pentylene, hexalene, heptalene, octalene, and an isomer thereof, and the like.

In the present invention, the C2-8 alkenylene group denotes ethynylene, propynylene, butenylene, pentenylene, hexenylene, heptenylene, octenylene, and an isomer thereof, and the like.

In the present invention, examples of the C1-4 alkoxy group include a methoxy group, an ethoxy group, a propoxy group, an isopropoxy group, a butoxy group, an isobutoxy group, a sec-butoxy group, or a tert-butoxy group.

In the present invention, the C2-4 alkenyloxy group denotes, for example, vinyloxy, propenyloxy, butenyloxy, and an isomer thereof, and the like.

In the present invention, the C2-4 alkynyloxy group denotes, for example, ethynyloxy, propynyloxy, butynyloxy, and an isomer thereof, and the like.

In the present invention, the C3-7 carbon ring denotes a C3-7 monocyclic carbon ring, and a carbon ring which may be partially or completely saturated, and examples thereof include cyclopropane, cyclobutane, cyclopentane, cyclohexane, cycloheptane, cyclobutene, cyclopentene, cyclohexene, cycloheptene, cyclobutadiene, cyclopentadiene, cyclohexadiene, cycloheptadiene, or benzene ring.

In the present invention, the C5-7 carbon ring denotes a C5-7 monocyclic carbon ring, and a carbon ring which may be partially or completely saturated, and examples thereof include cyclopentane, cyclohexane, cycloheptane, cyclopentene, cyclohexene, cycloheptene, cyclopentadiene, cyclohexadiene, cycloheptadiene, or benzene ring.

In the present invention, examples of the saturated C3-7 carbon ring include cyclopropane, cyclobutane, cyclopentane, cyclohexane, and cycloheptane.

In the present invention, the 4- to 10-membered heterocycle denotes 4- to 10-membered monocyclic or bicyclic heterocycle, which includes one to five heteroatoms selected from an oxygen atom, a nitrogen atom and a sulfur atom, and a part or all of which is saturated. Example thereof include azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxetane, dihydrofuran, tetrahydrofuran, dihydropyran, tetrahydropyran, dihydrooxepine, tetrahydrooxepine, perhydrooxepine, thietane, dihydrothiophene, tetrahydrothiophene, dihydrothiopyran, tetrahydrothiopyran, dihydrothiepin, tetrahydrothiepin, perhydrothiepin, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole, (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepin, tetrahydrothiadiazepin, perhydrothiadiazepin, morpholine, thiomorpholine, oxathiane, dioxolane, dioxane, dithiolane, dithiane, pyrrole, imidazole, triazole, tetrazole, pyrazole, pyridine, pyrazine, pyrimidine, pyridazine, azepine, diazepine, furan, pyran, oxepin, thiophene, thiopyran, thiepin, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepin, indole, isoindole, indolizine, benzofuran, isobenzofuran, benzothiophene, isobenzothiophene, indazole, purine, benzoxazole, benzothiazole, benzimidazole, benzofurazan, benzothiadiazole, benzotriazole, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydrobenzoxazole, perhydrobenzoxazole, dihydrobenzothiazole, perhydrobenzothiazole, dihydrobenzimidazole, perhydrobenzimidazole, dioxaindan, benzodithiolane, dithianaphthalene, quinoline, isoquinoline, quinolizine, phthalazine, pteridine, naphthyridine, quinoxaline, quinazoline, cinnoline, chromene, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, benzodioxan, chroman, or benzodithiane ring.

In the present invention, the 4- to 7-membered heterocycle denotes a 4- to 7-membered monocyclic heterocycle including one to five heteroatoms selected from an oxygen atom, a nitrogen atom and a sulfur atom and saturated partially or entirely. Examples thereof include azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxetane, dihydrofuran, tetrahydrofuran, dihydropyran, tetrahydropyran, dihydrooxepine, tetrahydrooxepine, perhydrooxepine, thietane, dihydrothiophene, tetrahydrothiophene, dihydrothiopyran, tetrahydrothiopyran, dihydrothiepin, tetrahydrothiepin, perhydrothiepin, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepin, tetrahydrothiadiazepin, perhydrothiadiazepin, morpholine, thiomorpholine, oxathiane, dioxolane, dioxane, dithiolane, dithiane, pyrrole, imidazole, triazole, tetrazole, pyrazole, pyridine, pyrazine, pyrimidine, pyridazine, azepine, diazepine, furan, pyran, oxepin, thiophene, thiopyran, thiepin, oxazole, isoxazole, thiazole, isothiazole, furazan, oxadiazole, oxazine, oxadiazine, oxazepine, oxadiazepine, thiadiazole, thiazine, thiadiazine, thiazepine, or thiadiazepin ring.

In the present invention, the 5- to 7-membered cyclic group denotes C5-7 carbon ring and 5- to 7-membered heterocycle. Herein, the C5-7 carbon ring has the same meaning as defined above, the 5- to 7-membered heterocycle includes 5- to 7-membered unsaturated heterocycle and 5- to 7-membered saturated heterocycle. Examples of 5- to 7-membered heterocycle include pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrofuran, tetrahydrofuran, dihydropyran, tetrahydropyran, dihydrooxepine, tetrahydrooxepine, perhydrooxepine, dihydrothiophene, tetrahydrothiophene, dihydrothiopyran, tetrahydrothiopyran, dihydrothiepin, tetrahydrothiepin, perhydrothiepin, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepin, tetrahydrothiadiazepin, perhydrothiadiazepin, morpholine, thiomorpholine, oxathiane, dioxolane, dioxane, dithiolane, dithiane, pyrrole, imidazole, triazole, tetrazole, pyrazole, pyridine, pyrazine, pyrimidine, pyridazine, azepine, diazepine, furan, pyran, oxepin, thiophene, thiopyran, thiepin, oxazole, isoxazole, thiazole, isothiazole, furazan, oxadiazole, oxazine, oxadiazine, oxazepine, oxadiazepine, thiadiazole, thiazine, thiadiazine, thiazepine, or thiadiazepin ring.

In the present invention, "when the C1-8 alkyl group represented by $R^1$ is a branched alkyl group, C1-3 alkyl groups branched from the same carbon atom may together form a saturated C3-7 carbon ring" denotes that in a partial structure of the following general formula (I):

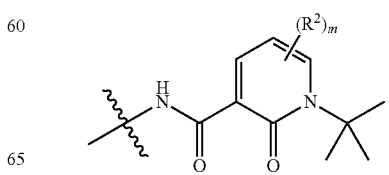

(wherein all of the symbols have the same meanings as defined above), for example, when R¹ is a branched alkyl chain as represented in the above-mentioned formula, the alkyl chain branched from the same carbon atom, together with the carbon atom bound thereto, forms a saturated carbon ring, as shown in the following formula:

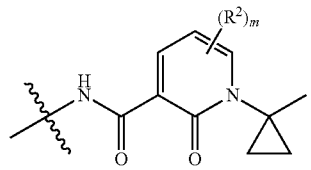

(wherein all of the symbols have the same meanings as defined above).

In the present invention, "R² is on adjacent carbon atoms and when R² represents a C1-3 alkyl group optionally substituted with an amino group, or a C2-3 alkenyl group optionally substituted with an amino group, R² bonded to the adjacent carbon atoms, together with the carbon atoms, may form a 5- to 7-membered cyclic group optionally substituted with one to three $R^{20}$" denotes that in a partial structure of the following general formula (I):

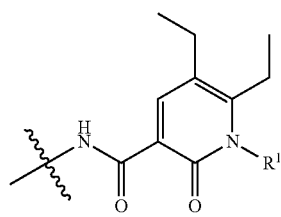

(wherein all of the symbols have the same meanings as mentioned above), for example, when a plurality of R² is an alkyl group shown in the above-mentioned formula, they, together with the adjacent carbon atoms, form a 5- to 7-membered cyclic group such as a cyclohexane ring followed by the following formula:

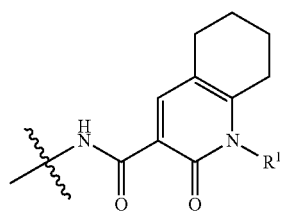

(wherein all of the symbols have the same meanings as mentioned above), or the like.

In the present invention, R¹ is preferably (1) a C1-8 alkyl group optionally substituted with one to five $R^{11}$, or (2) a C3-7 carbon ring optionally substituted with one to five $R^{12}$. Herein, the C3-7 carbon ring is preferably benzene.

In the present invention, R² is preferably a C1-8 alkyl group optionally substituted with one to five $R^{21}$, a C2-8 alkenyl group optionally substituted with one to five $R^{22}$, a C2-8 alkynyl group optionally substituted with one to five $R^{23}$, a halogen atom, or a C(O)$R^{27}$ group.

In the present invention, a ring represented by a formula that is a partial structure of the following general formula (I):

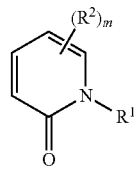

is preferably a ring represented by the following formula:

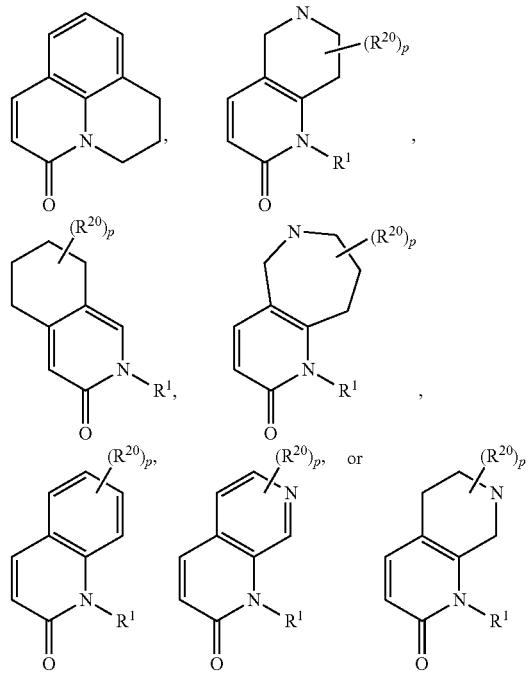

[wherein in the formula, p represents an integer of 0 to 3, and when p is two or more, a plurality of $R^{20}$ may be the same as or different from each other, and a nitrogen atom represents —NH— when $R^{20}$ is not substituted with the nitrogen atom, and the other symbols have the same meanings as defined above].

In the present invention, L is preferably —O—, —NH—, or —C(O)—, and more preferably —O—.

In the present invention, ring1 is preferably benzene or pyridine.

In the present invention, it is preferable that two binding arms in the ring1 are bound to a para position.

In the present invention, preferable compounds preferably include the compounds described in Examples, and more preferable examples include: (1) 5-acetyl-N-{5-[(6,7-dimethoxy-4-quinolinyl)oxy]-2-pyridinyl}-6-methyl-2-oxo-1-phenyl-1,2-dihydro-3-pyridinecarboxamide, (2) N-{5-[(6,7-dimethoxy-4-quinolinyl)oxy]-2-pyridinyl}-3,8-dioxo-2-phenyl-2,3,5,6,7,8-hexahydro-4-isoquinolinecarboxamide, (3) N-{5-[(6,7-dimethoxy-4-quinolinyl)oxy]-2-pyridinyl}-2,5-dioxo-1-phenyl-2,5,6,7,8,9-hexahydro-1H-pyrido[3,2-c]azepine-3-carboxamide, (4) 7-amino-N-{5-[(6,7-dimethoxy-4-quinolinyl)oxy]-2-pyridinyl}-2-oxo-1-phenyl-1,2-dihydro-3-quinolinecarboxamide, (5) N-{5-[(6,7-dimethoxy-4-quinolinyl)oxy]-2-pyridinyl}-2-oxo-1-phenyl-1,2-dihydro-1,7-naphthyridine-3-carboxamide, (6) 7-(2-butynoyl)-N-{5-[(6,7-dimethoxy-4-quinolinyl)oxy]-2-pyridinyl}-2-oxo-1-phenyl-1,2,5,6,7,8-hexahydro-1,7-naphthyridine-3-carboxamide.

[Isomer]

In the present invention, unless specifically directed, all of the isomers are included. For example, an alkyl group includes linear and branched chain groups. In addition, all of geometrical isomers of double bonds, rings, and fused rings (E-, Z-, cis-, trans-isomers), optical isomers by the presence of an asymmetric carbon atom (R-, S-isomer, α-, β-configurations, enantiomers, diastereomers), optical active isomers having optical rotation property (D, L, d, l-isomers), polar isomers according to chromatographic separation (more polar isomer, less polar isomer), equilibrium compound, rotamers, mixtures thereof at any rate, and racemic mixtures are included in the present invention. Furthermore, the present invention also encompasses all isomers by tautomers.

Furthermore, the optical isomer of the present invention is not only limited to an optical isomer having purity of 100%, but also may include other optical isomers having purity of less than 50%.

In the present invention, unless otherwise noted, as apparent to a person skilled in the art, a symbol:

represents binding toward the back side of the plane of the paper (that is to say, the α-configuration), represents binding toward the front side of the plane of the paper (that is to say, the β-configuration), and represents α-configuration, β-configuration or an arbitrary mixture thereof.

The compound represented by the general formula (I) is converted into a corresponding salt by the well-known method. A salt is preferably a water-soluble salt. Furthermore, the salt is pharmaceutically acceptable salt. Examples of a suitable salt include salts of an alkali metal (potassium, sodium, and the like), salts of an alkaline earth metal (calcium, magnesium, and the like), ammonium salts, or salts of a pharmaceutically acceptable organic amine (tetramethylammonium, triethylamine, methylamine, dimethylamine, cyclopentylamine, benzylamine, phenethylamine, piperidine, monoethanolamine, diethanolamine, tris(hydroxymethyl)aminomethane, lysine, arginine, N-methyl-D-glucamine, and the like), acid addition salts (inorganic acid salts (hydrochloride, hydrobromide, hydroiodide, sulfate, phosphate, nitrate, and the like), organic acid salts (acetate, trifluoroacetate, lactate, tartrate, oxalate, fumarate, maleate, benzoate, citrate, methanesulfonate, ethanesulfonate, benzenesulfonate, toluenesulfonate, isethionate, glucuronate, gluconate, and the like).

The compound represented by the general formula (I) and a salt thereof can be also converted into a solvate. It is preferable that the solvate is low-toxic and water-soluble. Examples of a suitable solvate include solvates with water, or an alcoholic solvent (for example, ethanol).

The N-oxide of the compound represented by the general formula (I) denotes compounds represented by the general formula (I) in which a nitrogen atom is oxidized. Furthermore, the N-oxide of the compound represented by the general formula (I) may be salts of alkali (alkaline earth) metal salt, ammonium salt, organic amine salt, and acid addition salt mentioned above.

The prodrug of the compound represented by the general formula (I) denotes a compound which is converted to a compound represented by the general formula (I) by a reaction with an enzyme, stomach acid, and the like, in a living body. Prodrugs of the compound represented by the general formula (I) include: compounds in which the hydroxyl group is acylated, alkylated, phosphorylated, or borated, when the compounds represented by the general formula (I) have a hydroxyl group (for example, the compounds represented by the general formula (I) in which the hydroxyl group is acetylated, palmitoylated, propanoylated, pivaloylated, succinylated, fumarylated, alanylated, or dimethylaminomethylcarbonylated); and compounds in which the carboxyl group is esterified or amidated (for example, compounds represented by the general formula (I) in which the carboxyl group is made into ethyl ester, isopropyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl) methyl ester, cyclohexyloxycarbonyl ethyl ester, methylamide, and the like). These compounds can be produced by well-known methods. Furthermore, the prodrug of the compound represented by the general formula (I) may be hydrate or non-hydrate. Furthermore, the prodrug of the compound represented by the general formula (I) may be a compound which is changed into the compound represented by the general formula (I) under the physiological condition, as described in "Development of Medicaments", vol. 7 "Molecular Design", p. 163-198, published by Hirokawa Shoten in 1990. In addition, the compound represented by the general formula (I) may be labeled with an isotope thereof (for example, $^2H$, $^3H$, $^{11}C$, $^{13}C$, $^{14}C$, $^{13}N$, $^{15}N$, $^{15}O$, $^{17}O$, $^{18}O$, $^{35}S$, $^{18}F$, $^{36}Cl$, $^{123}I$, $^{125}I$, and the like).

[Process for Producing Compound of the Present Invention]

The compound of the present invention can be produced by the well-known methods, for example, the method described in Comprehensive Organic Transformations: A Guide to Functional Group Preparations, 2nd Edition (Richard C. Larock, John Wiley & Sons Inc, 1999), or methods described in Examples, or the like, with appropriate modification and in combination thereof.

A compound represented by the general formula (I) wherein L is an oxygen atom, that is, a compound represented by general formula (I-A):

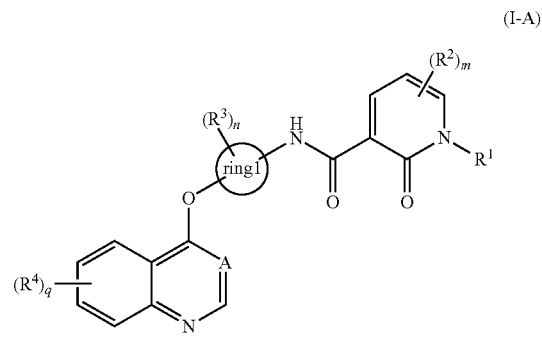

(I-A)

(wherein all of the symbols have the same meanings as defined above) can be produced by the process represented by the following reaction process schemes 1 and 2:

Reaction process scheme 1

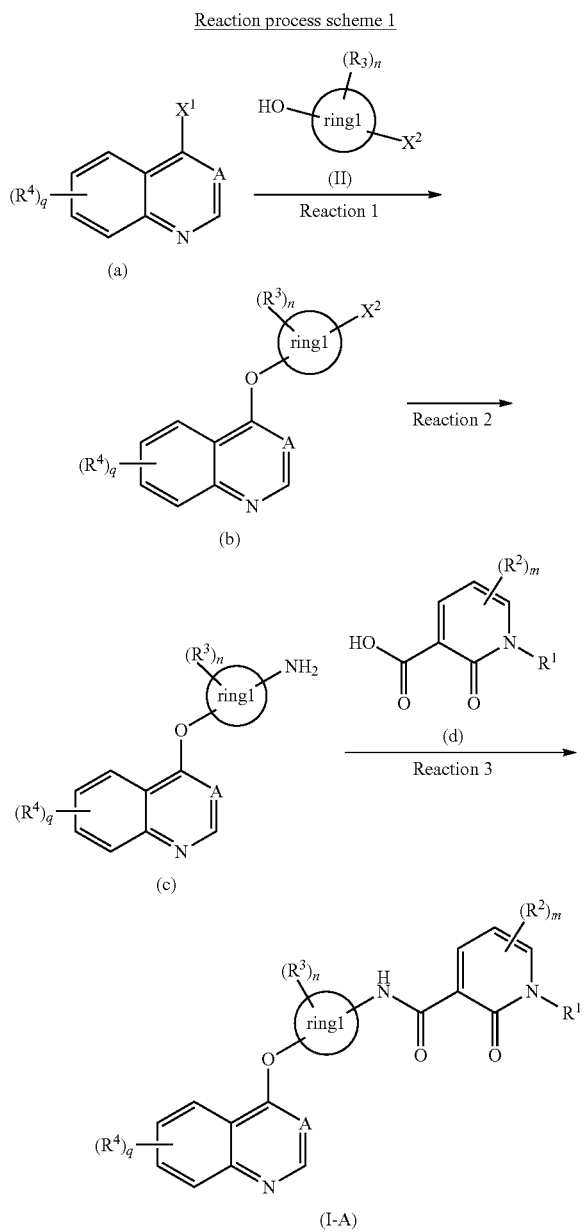

(wherein each of $X^1$ and $X^2$ independently represents a halogen atom, $X^1$ and $X^2$ may be the same as or different from each other, and the other symbols have the same meanings as defined above).

In the reaction process scheme 1, the reaction 1 can be carried out by using and subjecting a compound represented by general formula (a) and a compound represented by general formula (II) to the aromatic nucleophilic substitution reaction. The aromatic nucleophilic substitution reaction is well known, and is carried out, for example, in an organic solvent (chlorobenzene, N,N-dimethyl sulfoxide, N,N-dimethyl acetamide, N,N-dimethylformamide, chloroform, dichloromethane, diethyl ether, tetrahydrofuran, methyl t-butyl ether, and the like), in the presence of a catalyst (4-dimethylaminopyridine (DMAP) and the like), and in the presence or absence of a base (sodium hydride and the like), at 0 to 200° C.

In the reaction process scheme 1, the reaction 2 is carried out by reacting a compound represented by general formula (b) in an organic solvent (tetrahydrofuran, and the like), in the presence of a palladium catalyst (tris(dibenzylideneacetone)dipalladium(0) chloroform complex, and the like), in the presence of a base (lithium bis(trimethylsilyl)amide (LHMDS), potassium bis(trimethylsilyl)amide (KHMDS), sodium bis(trimethylsilyl)amide (NaHMDS), and the like), a phosphine compound (2-dicyclohexylphosphino-2',6'-dimethoxybiphenyl (S-Phos), tri-tert-butylphosphine (P(t-Bu)$_3$), and the like) at 0 to 100° C., and then reacting by adding inorganic acid (hydrochloric acid, hydrobromic acid, hydroiodic acid, sulfuric acid, phosphoric acid, nitric acid, and the like) at 0 to 150° C. Alternatively, the production method for aryl amine described in Organic Letters, Vol 3, No. 17, pp. 2729-2732, 2001 can be employed.

In the reaction process scheme 1, the reaction 3 can be carried out by using and subjecting the compound represented by general formula (c) and the compound represented by general formula (d) to an amidation reaction. The amidation reaction is well known, and examples thereof include:
(1) a method using an acid halide,
(2) a method using a mixed acid anhydride, and
(3) a method using a condensing agent.
These methods are specifically described below:
(1) The method using an acid halide is carried out, for example, by reacting a carboxylic acid with an acid halogenating agent (oxalyl chloride, thionyl chloride, and the like) in an organic solvent (chloroform, dichloromethane, diethyl ether, tetrahydrofuran, and the like) or in the absence of any solvent at −20° C. to reflux temperature, and then reacting the obtained acid halide in the presence of a base (pyridine, triethylamine, dimethylaniline, dimethylaminopyridine, diisopropylethylamine, and the like) in amine and an organic solvent (chloroform, dichloromethane, diethyl ether, tetrahydrofuran, and the like) at 0 to 40° C. Additionally, the method can be also carried out by reacting the obtained acid halide with an amine at 0 to 40° C. by using an alkaline aqueous solution (sodium bicarbonate water or sodium hydroxide solution, and the like) in an organic solvent (dioxane, tetrahydrofuran, and the like).

(2) The method using a mixed acid anhydride is carried out, for example, by reacting carboxylic acid with an acid halide (pivaloyl chloride, tosyl chloride, mesyl chloride, and the like) or an acid derivative (ethyl chloroformate, isobutyl chloroformate, and the like) in the presence of a base (pyridine, triethylamine, dimethylaniline, dimethylaminopyridine, diisopropylethylamine, and the like) in an organic solvent (chloroform, dichloromethane, diethyl ether, tetrahydrofuran, and the like) or in the absence of any solvent at 0 to 40° C., and then reacting the obtained mixed acid anhydride with amine in an organic solvent (chloroform, dichloromethane, diethyl ether, tetrahydrofuran, and the like) at 0 to 40° C.

(3) The method using a condensing agent is carried out, for example, by reacting a carboxylic acid with an amine in an organic solvent (chloroform, dichloromethane, dimethyl formamide, diethyl ether, tetrahydrofuran, and the like) or in the absence of any solvent at 0 to 40° C. in the presence or absence of a base (diisopropylethylamine (DIPEA), pyridine, triethylamine, dimethylaniline, dimethylaminopyridine, and the like), using a condensing agent (O-(7-aza-1-benzotriazolyl)-N,N,N',N'-tetramethyluronium hexafluorophosphate (HATU), (1,3-dicyclohexylcarbodiimide (DCC), 1-ethyl-3-[3-(dimethylamino)propyl]carbodiimide (EDC), 1,1'-carbonyldiimidazole (CDI), 2-chloro-1-methylpyridiniumiodine, 1-propylphosphonic acid cyclic anhydride (PPA), and the like) and using, or not using, 1-hydroxybenztriazole (HOBt).

These reactions (1), (2), and (3) are desirably carried out under an inert gas (argon, nitrogen, and the like) atmosphere in anhydrous conditions.

In the reaction process scheme 1, when a compound represented by each general formula includes a protective group, a deprotection reaction can be carried out if necessary. The deprotection reaction of the protective group is known, and can be carried out by the methods mentioned below. Examples thereof include: (1) deprotection reactions by alkaline hydrolysis, (2) deprotection reaction in acidic conditions, (3) deprotection reaction by hydrogenolysis, (4) deprotection reaction of a silyl group, (5) deprotection reaction using metal, (6) deprotection reaction using a metal complex, and the like.

These methods are specifically described:

(1) The deprotection reaction by alkaline hydrolysis condition is carried out, for example, in an organic solvent (for example, methanol, tetrahydrofuran, dioxane, etc.) with hydroxide of alkali metal (for example, sodium hydroxide, potassium hydroxide, lithium hydroxide, etc.), hydroxide of alkaline earth metal (for example, barium hydroxide, calcium hydroxide, and the like), or carbonate (for example, sodium carbonate or potassium carbonate, and the like), or an aqueous solution thereof or a mixture thereof at 0 to 40° C.

(2) The deprotection reaction in acidic conditions is carried out, for example, in an organic solvent (for example, dichloromethane, chloroform, dioxane, ethyl acetate, methanol, isopropyl alcohol, tetrahydrofuran, anisole, etc.), organic acid (for example, acetic acid, trifluoroacetic acid, methanesulfonic acid, p-tosyl acid, etc.), or inorganic acid (for example, hydrochloric acid, sulfuric acid, and the like), or a mixture thereof (for example, hydrogen bromide/acetic acid, and the like) in the presence or absence of 2,2,2-trifluoroethanol at 0 to 100° C.

(3) The deprotection reaction by hydrogenolysis is carried out, for example, in a solvent (for example, ethers (tetrahydrofuran, dioxane, dimethoxyethane, diethyl ether, etc.), alcohols (for example, methanol, ethanol, and the like), benzenes (for example, benzene, toluene, and the like), ketones (for example, acetone, methyl ethyl ketone, and the like), nitriles (for example, acetonitrile, and the like), amides (for example, N,N-dimethylformamide, and the like), water, ethyl acetate, acetic acid, or a mixture of two or more thereof, etc.) in the presence of a catalyst (for example, palladium-carbon, palladium black, palladium hydroxide-carbon, platinum oxide, Raney nickel, etc.) under a hydrogen atmosphere at normal pressure or elevated pressure, or in the presence of ammonium formate at 0 to 200° C.

(4) The deprotection reaction of a silyl group is carried out, for example, in a water-miscible organic solvent (for example, tetrahydrofuran, acetonitrile, and the like), by using tetrabutylammonium fluoride at 0 to 40° C. The reaction is also carried out, for example, in organic acid (for example, acetic acid, trifluoroacetic acid, methanesulfonic acid, p-tosyl acid, etc.), or in inorganic acid (for example, hydrochloric acid, sulfuric acid, and the like) or a mixture thereof (for example, hydrogen bromide/acetic acid, and the like) at −10 to 100° C.

(5) The deprotection reaction using a metal is carried out, for example, in an acidic solvent (for example, acetic acid, a buffer of pH 4.2 to 7.2, a mixed solution of the solution and an organic solvent such as tetrahydrofuran, and the like) in the presence of powder zinc, if necessary, with an ultrasonic wave applied at 0 to 40° C.

(6) The deprotection reaction using a metal complex is carried out, for example, in an organic solvent (for example, dichloromethane, N,N-dimethylformamide, tetrahydrofuran, ethyl acetate, acetonitrile, dioxane, ethanol, etc.), water or a mixed solvent thereof in the presence of a trap reagent (for example, tributyltin hydride, triethylsilane, dimedone, morpholine, diethylamine, pyrrolidine, etc.), an organic acid (for example, acetic acid, formic acid, 2-ethylhexanic acid, etc.) and/or in the presence of an organic acid salt (for example, sodium 2-ethylhexanate, potassium 2-ethylhexanate, etc.) in the presence or absence of a phosphine reagent (for example, triphenylphosphine, and the like) using a metal complex (for example, tetrakis(triphenylphosphine)palladium(O), dichlorobis(triphenylphosphine)palladium (II), palladium acetate (II), chlorotris(triphenylphosphine)rhodium (I), etc.) at 0 to 40° C.

In addition to the above-mentioned methods, the deprotection reaction can be carried out by the method described in for example, T. W. Greene, Protective Groups in Organic Synthesis, Wiley, New York, 1999.

Examples of a protective group for a hydroxyl group include a methyl group, a trityl group, a methoxymethyl (MOM) group, a 1-ethoxyethyl (EE) group, a methoxyethoxymethyl (MEM) group, a 2-tetrahydropyranyl (THP) group, a trimethylsilyl (TMS) group, a triethylsilyl (TES) group, a t-butyldimethylsilyl (TBDMS) group, a t-butyldiphenylsilyl (TBDPS) group, an acetyl (Ac) group, a pivaloyl group, a benzoyl group, a benzyl (Bn) group, a p-methoxybenzyl group, an allyloxycarbonyl (Alloc) group, a 2,2,2-trichloroethoxycarbonyl (Troc) group, and the like.

Examples of a protective group for an amino group include a benzyloxycarbonyl group, a t-butoxycarbonyl group, an allyloxycarbonyl (Alloc) group, a 1-methyl-1-(4-biphenyl)ethoxycarbonyl (Bpoc) group, a trifluoroacetyl group, a 9-fluororenylmethoxycarbonyl group, a benzyl (Bn) group, a p-methoxybenzyl group, a benzyloxymethyl (BOM) group, a 2-(trimethylsilyl)ethoxymethyl (SEM) group, and the like.

The protective groups for a hydroxyl group and an amino group are not particularly limited to the above-described groups, and groups are included, in addition to the above-mentioned groups, as long as the groups can be detached easily and selectively. For example, those described in T. W. Greene, Protective Groups in Organic Synthesis, Wiley, New York, 1999) may be used.

In each reaction in the present specification, compounds used as starting raw material, for example, the compound represented by general formula (a), (d), or (II) is well known or can be produced by well-known methods.

In each reaction in the present specification, as apparent to the skilled persons in the art, the reactions involving heating can be carried out using a water bath, an oil bath, a sand bath or a microwave.

In each reaction in the present specification, a solid-supported reagent which is supported on a high molecular polymer (e.g., polystyrene, polyacrylamide, polypropylene, polyethylene glycol, etc.) may be appropriately used.

In each reaction in the present specification, the reaction products can be purified by conventional purification methods, for example, by distillation at normal or reduced pressure, by high performance liquid chromatography using silica gel or magnesium silicate, thin layer chromatography, ion-exchange resin, scavenger resin, or column chromatography, washing, recrystallization, or the like. The purification may be done after each reaction or after several reactions.

[Toxicity]

The toxicity of the compound of the present invention is sufficiently low, and the compound can be safely used as pharmaceuticals.

[Application to Pharmaceuticals]

Since the compound of the present invention has an Axl inhibitory activity, it can be used as an agent for preventing and/or treating an Axl-related disease in mammals, especially in human.

In the present invention, examples of the Axl-related diseases include cancer, kidney diseases, immune system disease, and circulatory system disease.

In the present invention, the cancer includes acute myeloid leukemia, chronic myeloid leukemia, acute lymphatic leukemia, chronic lymphatic leukemia, multiple myeloma, melanoma, breast cancer, pancreatic cancer, glioma, esophageal adenocarcinoma, large intestine cancer, renal cell carcinoma, thyroid cancer, non-small cell lung cancer, prostate cancer, stomach cancer, uveal malignant melanoma, ovarian cancer, endometrial cancer, lymphoma, head and neck cancer, liver cancer, and sarcoma.

In the present invention, examples of the kidney diseases include glomerular nephritis, chronic nephritis, IgA nephritis, sequential (secondary) nephritis, nephrosis nephritis, acute renal failure, chronic renal failure, diabetic nephropathy, gouty nephropathy, interstitial nephritis, and nephropyelitis.

In the present invention, examples of the immune system disease include psoriasis, and rheumatoid arthritis.

In the present invention, examples of the circulatory system disease include atherosclerosis and thrombosis.

Furthermore, since the compound of the present invention has an Axl inhibitory activity, it can be used as a metastasis suppressing agent to tumor cells.

The compound of the present invention may be administered as a combination drug in combination with other drugs in order to accomplish the following purposes:
1) to supplement and/or enhance the preventive and/or therapeutic effect of the compound;
2) to improve the kinetics, improvement of absorption, and reduction of the dose of the compound; and/or
3) to eliminate the side effects of the compound.

A combination drug of the compound of the present invention and other drugs may be administered in the form of a compounding agent including these components mixed into one formulation, or may be administered in separate formulations. Administration as separate formulations includes simultaneous administration and administration at different times. In the administration at different times, the compound of the present invention may be administered before the other drug. Alternatively, the other drug may be administered before the compound of the present invention. The method for the administration of these drugs may be the same as each other or different from each other.

Diseases on which the preventive and/or therapeutic effect of the above-mentioned combination drug works are not particularly limited but may be those in which the preventive and/or therapeutic effect of the compound of the present invention is supplemented and/or enhanced.

The other drugs for supplementing and/or enhancing the preventive and/or therapeutic effect of the compound of the present invention against cancer include, for example, alkylating agents, antimetabolites, anticancer antibiotics, plant alkaloids, hormones, platinum compounds, anti-CD20 antibodies, anti-CD52 antibodies, G-CSF formulations, acute promyelocytic leukemia differentiation-inducing agents, kinase inhibitors, topoisomerase inhibitors, aromatase inhibitors, and other anticancer drugs.

The other drug for supplementing and/or enhancing the preventive and/or therapeutic effect of the compound of the present invention against kidney diseases include, for example, steroids, immunosuppressants, angiotensin II antagonistic drugs, angiotensin-converting enzyme inhibitors, antiplatelet drugs, and anticoagulant drugs.

The other drugs for supplementing and/or enhancing the preventive and/or therapeutic effect of the compound of the present invention against immune system diseases include, for example, immunosuppressants; steroids; disease-modifying anti-rheumatic drugs; prostaglandins; prostaglandin synthase inhibitors; phosphodiesterase inhibitors; metalloprotease inhibitors; anti-cytokine protein formulations such as anti-TNF-α formulations, anti-IL-1 formulations, and anti-IL-6 formulation; cytokine inhibitors; and nonsteroidal anti-inflammatory agents.

The other drugs for supplementing and/or enhancing the preventive and/or therapeutic effect of the compound of the present invention against circulatory system diseases include antiplatelet drugs, angiotensin II antagonistic drugs, angiotensin-converting enzyme inhibitors, HMG-CoA reductase inhibitors, and thiazolidine derivatives.

Examples of the alkylating agents include nitrogen mustard N-oxide hydrochloride, cyclophosphamide, ifosfamide, melphalan, thiotepa, carboquone, busulfan, nimustine hydrochloride, dacarbazine, ranimustine, carmustine, chlorambucil, bendamustine, and mechlorethamine.

Examples of the antimetabolites include methotrexate, mercaptopurine, 6-mercaptopurine riboside, fluorouracil, tegafur, tegafur uracil, carmofur, doxifluridine, cytarabine, enocitabine, tegafur gimestat otastat potassium, gemcitabine hydrochloride, cytarabine ocfosfate, procarbazine hydrochloride, and hydroxycarbamide.

Examples of the anticancer antibiotics include actinomycin D, mitomycin C, daunorubicin hydrochloride, doxorubicin hydrochloride, aclarubicin hydrochloride, neocarzinostatin, pirarubicin hydrochloride, epirubicin (hydrochloride), idarubicin hydrochloride, chromomycin A3, bleomycin (hydrochloride), peplomycin sulfate, therarubicin, zinostatin stimalamer, gemtuzumab ozogamicin, and the like.

Examples of the plant formulations include vinblastine sulfate, vincristine sulfate, vindesine sulfate, irinotecan hydrochloride, etoposide, flutamide, vinorelbine tartrate, docetaxel hydrate, paclitaxel, and the like.

Examples of the hormones include estramustine phosphate sodium, mepitiostane, epitiostanol, goserelin acetate, fosfestrol (diethylstilbestrol phosphate), tamoxifen citrate, toremifene citrate, fadrozole hydrochloride hydrate, medroxyprogesterone acetate, bicalutamide, leuprorelin acetate, anastrozole, aminoglutethimide, androgen bicalutamide, fulvestrant, and the like.

Examples of the platinum compounds include carboplatin, cisplatin, nedaplatin, and oxaliplatin, and the like.

Examples of the anti-CD20 antibodies include rituximab, ibritumomab, ibritumomab tiuxetan, and ocrelizumab.

Examples of the anti-CD52 antibodies include alemtuzumab.

Examples of the G-CSF formulation include pegfilgrastim, filgrastim, lenograstim, and nartograstim.

Examples of the differentiation-inducing agent for acute promyelocytic leukemia include tamibarotene, tretinoin, and arsenic trioxide formulations.

Examples of the kinase inhibitors include EGFR inhibitors including erlotinib hydrochloride, gefitinib, cetuximab, and panitumumab; HER2 inhibitors including lapatinib and trastuzumab; BCR-ABL inhibitors including imatinib, dasatinib, and nilotinib; multikinase inhibitors including sunitinib, vandetanib, crizotinib, and sorafenib.

Examples of the topoisomerase inhibitor include topotecan, teniposide, irinotecan, and sobuzoxane.

Examples of the aromatase inhibitor include exemestane.

Examples of the other anticancer agents include L-asparaginase, octreotide acetate, porfimer sodium, mitoxantrone acetate, aceglatone, ubenimex, eribulin mesilate, cladribine, krestin, bexarotene, denileukin diftitox, temozolomide, nelarabine, fludarabine, bevacizumab, pemetrexed, pentostatin, bortezomib, lenalidomide, and calcium folinate.

Examples of the immunosuppressant include azathioprine, ascomycin, everolimus, salazosulfapyridine, cyclosporine, cyclophosphamide, sirolimus, tacrolimus, bucillamine, methotrexate, and leflunomide.

Examples of the steroid include amcinonide, hydrocortisone sodium succinate, prednisolone sodium succinate, methylprednisolone sodium succinate, ciclesonide, difluprednate, betamethasone propionate, dexamethasone, deflazacort, triamcinolone, triamcinolone acetonide, halcinonide, dexamethasone palmitate, hydrocortisone, flumetasone pivalate, prednisolone butylacetate, budesonide, prasterone sulfate, mometasone furoate, fluocinonide, fluocinolone acetonide, fludroxycortide, flunisolide, prednisolone, alclometasone propionate, clobetasol propionate, dexamethasone propionate, deprodone propionate, fluticasone propionate, beclometasone propionate, betamethasone, methylprednisolone, methylprednisolone suleptanate, methylprednisolone sodium succinate, dexamethasone sodium phosphate, hydrocortisone sodium phosphate, prednisolone sodium phosphate, diflucortolone valerate, dexamethasone valerate, betamethasone valerate, prednisolone valerate acetate, cortisone acetate, diflorasone acetate, dexamethasone acetate, triamcinolone acetate, paramethason acetate, halopredone acetate, fludrocortisone acetate, prednisolone acetate, methylprednisolone acetate, clobetasone butyrate, hydrocortisone butyrate, hydrocortisone butyrate propionate, and betamethasone butyrate propionate.

Examples of the angiotensin II antagonistic drug include losartan, candesartan, valsartan, irbesartan, olmesartan, telmisartan, and the like.

Examples of the angiotensin-converting enzyme inhibitor include alacepril, imidapril hydrochloride, quinapril hydrochloride, temocapril hydrochloride, delapril hydrochloride, benazepril hydrochloride, captopril, trandolapril, perindopril erbumine, enalapril maleate, lisinopril, and the like.

Examples of the antiplatelet drugs include dipyridamole, and dilazep hydrochloride hydrate.

Examples of the anticoagulant drugs include warfarin and heparin.

Examples of the disease-modifying anti-rheumatic drugs include D-penicillamine, actarit, auranofin, salazosulfapyridine, hydroxychloroquine, bucillamine, methotrexate, leflunomide, lobenzarit sodium, aurothioglucose, and sodium aurothiomalate.

Examples of the prostaglandins (hereinafter, abbreviated as "PG") include PGE1 formulations (examples: alprostadil alfadex, alprostadil), PGI2 formulations (example: beraprost sodium), PG receptor agonists, and PG receptor antagonists. Examples of the PG receptor include PGE receptors (EP1, EP2, EP3, and EP4), PGD receptors (DP, and CRTH2), PGF receptors (FP), PGI2 receptors (IP), and TX receptors (TP).

Examples of the prostaglandin synthase inhibitor include salazosulfapyridine, mesalazine, olsalazine, 4-aminosalicylic acid, JTE-522, auranofin, carprofen, diphenpyramide, flunoxaprofen, flurbiprofen, indometacin, ketoprofen, lornoxicam, loxoprofen, meloxicam, oxaprozin, parsalmide, piproxen, piroxicam, piroxicam cinnamate, zaltoprofen, and pranoprofen.

Examples of the phosphodiesterase inhibitor include rolipram, cilomilast, Bay19-8004, NIK-616, roflumilast (BY-217), cipamfylline (BRL-61063), atizoram (CP-80633), ONO-6126, SCH-351591, YM-976, V-11294A, PD-168787, D-4396, and IC-485.

Examples of the anti-TNF-α formulation include anti-TNF-α antibodies, soluble TNF-α receptor, anti-TNF-α receptor antibodies, and soluble TNF-α binding protein, and particularly infliximab and etanercept.

Examples of the anti-IL-1 formulation include anti-IL-1 antibodies, soluble IL-1 receptor, anti-IL-1Ra antibodies and/or anti-IL-1 receptor antibodies and particularly anakinra.

Examples of the anti-IL-6 formulation include anti-IL-6 antibodies, soluble IL-6 receptor, and anti-IL-6 receptor antibodies, and particularly tocilizumab.

Examples of the cytokine inhibitor include suplatast tosylate, T-614, SR-31747, and sonatimod.

Examples of the HMG-CoA reductase inhibitor include atorvastatin, fluvastatin, lovastatin, pitavastatin, pravastatin, rosuvastatin, and simvastatin.

Examples of the thiazolidine derivative include pioglitazone, ciglitazone, rosiglitazone, and troglitazone.

Furthermore, the combination drugs to be combined with a compound of the present invention includes not only ones discovered to date, but also ones that may be discovered in the future.

The compound of the present invention is usually administered systemically or locally, by oral or parenteral administration. Examples of oral agents include liquid medicines for internal use (for example, elixirs, syrups, pharmaceutically acceptable water-based agents, suspensions, and emulsions), and solid medicine for internal use (for example, tablets (including sublingual tablets and orally disintegrating tablets), pills, capsules (including hard capsules, soft capsules, gelatin capsules, and microcapsules), powders, granules, and lozenges). Examples of parenteral agents include liquid medicines (for example, injection agents (for example, subcutaneous injection agents, intravenous injection agents, intramuscular injection agents, intraperitoneal injection agents, and drip agents), eye drops (for example, aqueous eye drops (aqueous eye drops, aqueous eye drop suspensions, viscous eye drops, and solubilized eye drops, etc.), and nonaqueous eye drops (for example, nonaqueous eye drops and nonaqueous eye drop suspensions), and the like), agents for external use (for example, ointments (ophthalmic ointments, and the like)), and ear-drops, and the like. These formulations may be controlled release agents such as rapid release formulations, sustained release formulations, and the like. These formulations can be produced by well-known methods, for example, by the methods described in The Japanese Pharmacopoeia.

Liquid medicines for internal use as the oral agent can be produced by, for example, dissolving or suspending an active ingredient in a generally used diluent (for example, purified water, ethanol, or mixture liquid thereof, or the like). The liquid medicine may include a wetting agent, a suspension agent, an emulsifying agent, a sweetening agent, a flavoring material, an aromatic substance, a preservative, a buffer agent, and the like.

Solid medicines for internal use as the oral agent are formulated by, for example, mixing the active ingredient with, for example, a vehicle (for example, lactose, mannitol, glucose, microcrystalline cellulose, and starch), a binder (for example, hydroxypropyl cellulose, polyvinylpyrrolidone, and magnesium metasilicate aluminate), a disintegrant (for example, sodium carboxymethylcellulose), a lubricant (for example, magnesium stearate), a stabilizer, a dissolution adjuvant (for example, glutamic acid and aspartic acid), and the like, and formulating according to standard methods. As necessary, coating may be carried out with a coating agent (for example, sugar, gelatin, hydroxypropyl cellulose, and hydroxypropyl methyl cellulose phthalate), and coating of two or more layers may be employed.

Agents for external use as parenteral agents are produced by well-known methods or generally used prescriptions. For example, an ointment may be produced by incorporation or melting of an active ingredient into base material. The ointment base material is selected from well-known material or generally used material. For example, a single material or a mixture of two or more of materials are selected from higher fatty acids and higher fatty acid esters (for example, adipic acid, myristic acid, palmitic acid, stearic acid, oleic acid, adipate esters, myristate esters, palmitate esters, stearate esters, and oleate esters), waxes (for example, beeswax, spermaceti, and ceresin), surfactants (for example, polyoxyethylene alkyl ether phosphate esters), higher alcohols (for example, cetanol, stearyl alcohol, and cetostearyl alcohol), silicone oils (for example, dimethylpolysiloxane), hydrocarbons (for example, hydrophilic petrolatum, white petrolatum, purified lanolin, and liquid paraffin), glycols (for example, ethylene glycol, diethylene glycol, propylene glycol, polyethylene glycol, and macrogol), plant oils (for example, castor oil, olive oil, sesame oil, and turpentine oil), animal oils (for example, mink oil, egg yolk oil, squalane, and squalene), water, absorption promoters, and anti-irritants. Furthermore, a humectant, preservative, stabilizer, antioxidant, fragrance, and the like, may be included.

The injection agents as parenteral agents include solutions, suspensions, emulsions and solid injection agents to be dissolved or suspended in a solvent before use. The injection agent is used by, for example, dissolving, suspending or emulsifying an active ingredient in a solvent. Examples of the solvent include distilled water for injection, physiological saline, vegetable oils, alcohols such as propylene glycol, polyethylene glycol, ethanol, and mixtures thereof. Furthermore, the injection agent may contain a stabilizer, a dissolution aid (glutamic acid, aspartic acid, and Polysorbate 80 (registered trademark), etc.), a suspending agent, an emulsifying agent, a soothing agent, a buffer, a preservative, and the like. Such an injection agent is produced by sterilizing at the final step or employing an aseptic process. Furthermore, it is also possible to employ an aseptic solid product such as a freeze-dried product produced and sterilized or dissolved in aseptic distilled water for injection or other solvent before use.

When the compound of the present invention or combination agents of the compound of the present invention and other agents are used for the above-mentioned purposes, they are usually administered systemically or locally, usually by oral or parenteral administration. The doses to be administered are different depending upon ages, body weights, symptoms, therapeutic effects, administration method, treatment time, and the like. The doses per adult person are generally from 1 ng to 1000 mg per dose, once or several times per day, by oral administration, from 0.1 ng to 100 mg per dose, once or several times per day, by parenteral administration, or continuous administration 1 to 24 hours per day intravenously. Needless to say, as mentioned above, the doses to be used vary dependent upon various conditions. Therefore, doses lower than the ranges specified above may be sufficient in some cases, and doses higher than the ranges specified above are needed in some cases.

EXAMPLES

Hereinafter, the present invention is described in detail with reference to Examples mentioned below, but the present invention is not limited thereto.

Solvents given in parentheses shown in chromatographic separation and TLC each indicate the elution solvent or the developing solvent used, and the ratio is expressed in ratio by volume. The description "NH silica" denotes that CHROMATOREX NH TLC PLATE (catalog No.; 3800003) manufactured by FUJI SILYSIA CHEMICAL LTD was used; and "DNH silica" denotes that CHROMATOREX NH TLC PLATE (catalog No.; 3800403) manufactured by FUJI SILYSIA CHEMICAL LTD was used.

LC-MS/ELSD was carried out in the following conditions:

{Column: Waters ACQUITY $C_{18}$ (particle diameter: $1.7 \times 10^{-6}$ m; column length: 30×2.1 mm I.D.); flow rate: 1.0 mL/min; column temperature: 40° C.; mobile phase (A): 0.1% formic acid aqueous solution; mobile phase (B): 0.1% formic acid-acetonitrile solution; gradient (rate of mobile phase (A):mobile phase (B)): [0 min] 95:5; [0.1 min] 95:5; [1.2 min] 5:95; [1.4 min] 5:95; [1.41 min] 95:5; [1.5 min] 95:5; detector: UV (PDA), ELSD, MS}.

The description in a parenthesis in the NMR data shows a solvent used for measurement.

Name of the compounds used in this specification are named by using ACD/Name (registered trademark) manufactured by Advanced Chemistry Development Inc., which is a computer program for naming compounds according to the regulation of IUPAC, or named according to the naming method of IUPAC.

Example 1: 4-[(6-chloro-3-pyridinyl)oxy]-6,7-dimethoxy quinoline

Under a stream of nitrogen, a solution of 4-chloro-6,7-dimethoxy quinoline (39 g) (CAS registration No.: 35654-56-9) in chlorobenzene (400 mL), 6-chloropyridine-3-ol (25 g), and 4-dimethylaminopyridine (DMAP) (64 g) were placed into a 2-L four-necked flask, and the mixture was stirred at a bath temperature (140° C.) for 42 hours. The resulting solution was allowed to cool to room temperature, water (700 mL) and ethyl acetate (1 L) were added thereto, and the solution was separated. The water layer was extracted again with ethyl acetate (1 L). The combined organic layer was washed with a saturated saline solution (500 mL), and dried over anhydrous sodium sulfate, and a solvent was removed by evaporation under reduced pressure. The resulting residue was purified by silica gel column chromatography (hexane:ethyl acetate=1:8) to obtain the title compound (28 g) having the following physical property values.

TLC: Rf 0.22 (hexane:ethyl acetate=1:3);
$^1$H-NMR (DMSO-$d_6$): δ 8.52, 8.48, 7.87-7.85, 7.66, 7.49, 7.43, 6.65, 3.95, 3.93.

Example 2: 5-[(6,7-dimethoxy-4-quinolinyl)oxy]-2-pyridinamine

Under a stream of nitrogen, a tetrahydrofuran (THF) solution (500 mL) of the compound (28 g) produced in Example 1, 1.3 mol/L lithium bis(trimethylsilyl)amide (LHDMS) (100 mL), tris(dibenzylideneacetone)dipalladium(0) chloroform complex (4.6 g), and 2-dicyclohexylphosphino-2',6'-dimethoxybiphenyl (4.4 g) were placed into a 2-L four-necked flask. The mixture was stirred at a bath temperature (80° C.) for two hours. Furthermore, 6 mol/L hydrochloric acid (250 mL) was added thereto, and the mixture was stirred at a bath temperature (80° C.) for two hours. The mixture was allowed to cool to room temperature, then filtered through celite (washed with 2 L of ethyl acetate), then a saturated sodium hydrogen bicarbonate aqueous solution (2 L) was added, and the resulting solution was separated. The water layer was extracted again with ethyl acetate (1 L). The combined organic layer was washed with a saturated saline solution (500 mL), and then dried over anhydrous sodium sulfate. A solvent was removed by evaporation under reduced pressure. The resulting residue was purified by silica gel column chromatography (ethyl acetate→ethyl acetate:methanol=9:1) to obtain the title compound (22 g) having the following physical property values.

TLC: Rf 0.51 (ethyl acetate:methanol=4:1);

$^1$H-NMR (DMSO-d$_6$): δ 8.45, 7.89, 7.51, 7.38-7.36, 6.56, 6.42, 6.05, 3.94.

Example 3

N-{5-[(6,7-dimethoxy-4-quinolinyl)oxy]-2-pyridinyl}-2-oxo-1-phenyl-1,2-dihydro-3-pyridinecarboxamide 2-oxo-1-phenyl-1,2-dihydropyridine-3-carboxylic acid (CAS registration No: 868171-81-7) (1.9 g) and O-(7-aza-1-benzotriazolyl)-N,N,N',N'-tetramethyl uronium hexafluorophosphate (HATU) (4.1 g) were dissolved in N,N-dimethyl formamide (DMF) (50 mL) at room temperature, and diisopropyl ethylamine (DIPEA) (2.3 g) and the compound (2.7 g) produced in Example 2 were added thereto. The mixture was stirred for 21 hours. Water was added to the reaction solution to precipitate a solid. The solid obtained by filtration was washed with ethanol. The resulting residue was dried under reduced pressure to obtain the title compound (3.6 g) having the following physical property values.

TLC: Rf 0.54 (ethyl acetate:methanol=9:1);

$^1$H-NMR (CDCl$_3$): δ 4.05, 6.46, 6.59, 7.41-7.44, 7.51-7.57, 7.68, 8.26, 8.48, 8.51, 8.74, 12.40.

Examples 3(1) to 3(2)

The compound produced in Example 2 and a corresponding carboxylic acid derivative in place of 2-oxo-1-phenyl-1,2-dihydropyridine-3-carboxylic acid were used and subjected to the procedure having the same purpose as in Example 3 to obtain the compounds of the following Examples.

Example 3(1)

N-{5-[(6,7-dimethoxy-4-quinolinyl)oxy]-2-pyridinyl}-5-oxo-2,3-dihydro-1H,5H-pyrido[3,2,1-ij]quinoline-6-carboxamide TLC: Rf 0.66 (ethyl acetate:methanol=5:1);

$^1$H-NMR (CDCl$_3$): δ 2.11, 3.00, 3.94, 4.23, 6.56, 7.32, 7.41, 7.54, 7.60, 7.87-7.94, 8.41-8.50, 9.04, 12.76.

Example 3(2)

N-{5-[(6,7-dimethoxy-4-quinolinyl)oxy]-2-pyridinyl}-4,6-dimethyl-2-oxo-1-phenyl-1,2-dihydro-3-pyridinecarboxamide TLC: Rf 0.64 (ethyl acetate:methanol=19:1);

$^1$H-NMR (CDCl$_3$): δ 2.05, 2.81, 4.05, 6.26, 6.43, 7.22, 7.42, 7.49-7.59, 8.21, 8.41, 8.49, 12.50.

Example 4: Methyl 5-acetyl-6-methyl-2-oxo-1,2-dihydropyridine-3-carboxylate 5-acetyl-6-methyl-2-oxo-1,2-dihydropyridine-3-carboxylic acid (CAS registration No: 88302-06-1) (450 mg) was dissolved in methanol (20 mL), and oxalyl chloride (0.43 mL) was dripped thereto at 0° C. The mixture was stirred at room temperature for three hours. The reaction solution was concentrated under reduced pressure. Saturated sodium hydrogen carbonate was added to the resultant residue, followed by extraction with dichloromethane. The organic layer was dried over sodium sulfate, filtered, and then concentrated under reduced pressure to obtain the title compound (400 mg) having the following physical property values.

$^1$H-NMR (CDCl$_3$): δ 2.54, 2.79, 3.94, 8.72, 12.34.

Example 5: 5-acetyl-6-methyl-2-oxo-1-phenyl-1,2-dihydropyridine-3-carboxylic acid The compound (500 mg) produced in Example 4, phenylboronic acid (580 mg), diacetoxycopper (II) (870 mg), pyridine (5.0 mL) and 4 Å molecular sieve (1.0 g) were added to dichloromethane (10 mL). The mixture was stirred under an oxygen atmosphere at room temperature for 48 hours. The reaction solution was filtered through celite to remove insoluble solids, and then diluted by the addition of dichloromethane (200 mL). The organic layer was washed with water. The resulting organic layer was dried over sodium sulfate, and filtered. Then, the solvent was concentrated under reduced pressure and removed by evaporation. THF (20 mL), methanol (1 mL) and lithium hydroxide monohydrate (91 mg) were added to the resulting residue and the mixture was stirred at room temperature for 16 hours. To the reaction solution, 1 mol/L hydrochloric acid was added. The organic layer was extracted with dichloromethane (3×50 mL), and dried over magnesium sulfate and filtered, and then concentrated under reduced pressure to obtain the title compound (46 mg) having the following physical property values.

$^1$H-NMR (CDCl$_3$): δ 2.45, 2.64, 7.17-7.20, 7.57-7.64, 8.98, 13.44.

Example 6

5-acetyl-N-{5-[(6,7-dimethoxy-4-quinolinyl)oxy]-2-pyridinyl}-6-methyl-2-oxo-1-phenyl-1,2-dihydro-3-pyridinecarboxamide

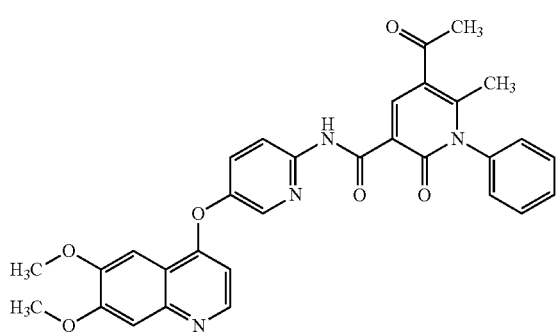 [SMILES: COc1cc2nccc(Oc3ccc(NC(=O)c4cc(C(C)=O)c(C)n(-c5ccccc5)c4=O)nc3)c2cc1OC]

The compound (20 mg) produced in Example 5 and the compound (20 mg) produced in Example 2 were used and subjected to the procedure having the same purpose as in Example 3 to obtain the title compound (12 mg) having the following physical property values.

(LC-MS/ELSD): (retention time: 0.81 min);
$^1$H-NMR (CDCl$_3$): δ 2.45, 2.67, 4.04, 4.05, 6.46, 7.21, 7.42, 7.53-7.64, 8.24, 8.46, 8.51, 9.12, 12.04.

Example 7: 4-[(6-chloro-3-pyridinyl)oxy]-6,7-dimethoxy quinazoline

Under an argon atmosphere, DMAP (4.4 g) was added to a DMSO suspension (20 mL) of 4-chloro-6,7 dimethoxy quinazoline (CAS registration No: 13790-39-1) (8.0 g) and 6-chloropyridine-3-ol (4.6 g), and the mixture was heated and stirred at a bath temperature (80° C.) for two hours. The mixture was allowed to cool to room temperature. The reaction solution was diluted with ethyl acetate, and washed with water and a saturated sodium hydrogen carbonate aqueous solution. The organic layer was dried over anhydrous sodium sulfate and concentrated, and the resulting residue was washed with hexane-ethyl acetate (3:1) to obtain the title compound (9.1 g) having the following physical property values.

TLC: Rf 0.16 (hexane:ethyl acetate=1:1);
$^1$H-NMR (DMSO-d$_6$): δ 3.97, 3.99, 7.41, 7.58, 7.69, 7.97, 8.50, 8.57.

Example 8: 5-[(6,7-dimethoxy-4-quinazolinyl)oxy]-2-pyridinamine hydrochloride Under an argon atmosphere, 1.0 mol/L LHDMS (4.7 mL), tris(dibenzylideneacetone)dipalladium(0) chloroform complex (140 mg), and 2-dicyclohexylphosphino-2',6'-dimethoxybiphenyl (170 mg) were added to a THF solution (15 mL) of the compound (1.0 g) produced in Example 7. The mixture was stirred at a bath temperature (70° C.) for four hours. After the reaction solution was allowed to cool to room temperature, and placed into ice water, followed by extraction with ethyl acetate. The organic layer was washed with water, dried over anhydrous sodium sulfate, and concentrated. The resulting residue was suspended in acetonitrile (30 mL), and 2.0 mol/L hydrochloric acid (10 mL) was added thereto. The mixture was stirred at room temperature for 30 min. Precipitates generated in the reaction solution were collected by filtration to obtain the title compound (1590 mg) having the following physical property values.

TLC: Rf 0.16 (ethyl acetate:methanol=10:1);
$^1$H-NMR (DMSO-d$_6$): δ 3.96, 3.99, 4.24, 7.10, 7.42, 7.53, 8.00-8.20, 8.07, 8.20, 8.61.

Example 9

5-acetyl-N-{5-[(6,7-dimethoxy-4-quinazolinyl)oxy]-2-pyridinyl}-6-methyl-2-oxo-1-phenyl-1,2-dihydro-3-pyridinecarboxamide

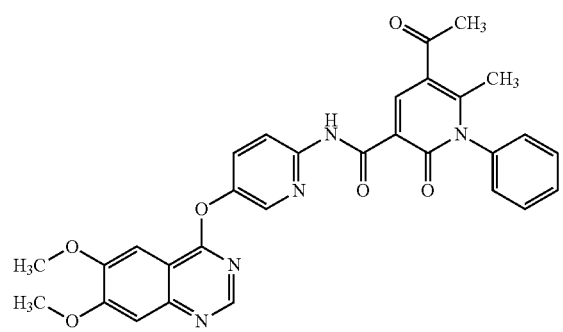 [SMILES: COc1cc2ncnc(Oc3ccc(NC(=O)c4cc(C(C)=O)c(C)n(-c5ccccc5)c4=O)nc3)c2cc1OC]

The compound (25 mg) produced in Example 5 and the compound (28 mg) produced in Example 8 were used and subjected to the procedure having the same purpose as in Example 3 to obtain the title compound (14 mg) having the following physical property values.

(LC-MS/ELSD): (retention time: 0.95 min);
$^1$H-NMR (CDCl$_3$): δ 2.45, 2.68, 4.07, 7.19-7.23, 7.33, 7.54, 7.55-7.65, 7.68, 8.28, 8.48, 8.61, 9.12, 12.02.

Example 10: 2,2-dimethyl propyl 5-bromo-2-oxo-1-phenyl-1,2-dihydropyridine-3-carboxylate To dichloromethane (60 mL), 2,2-dimethyl propyl 5-bromo-2-hydroxypyridine-3-carboxylate (2.0 g) was used and phenylboronic acid (1.7 g), diacetoxycopper(II) (5.2 g), and pyridine (15 mL) were added. The mixture was stirred under an oxygen atmosphere at room temperature for 16 hours. The reaction solution was filtered through celite to remove insoluble solids, and diluted by the addition of dichloromethane. The organic layer was washed with water and 1 mol/L hydrochloric acid. The resulting organic layer was dried over sodium sulfate, filtered, and concentrated under reduced pressure. Then, a solvent was removed by evaporation under reduced pressure to obtain the title compound (1.5 g) having the following physical property value.

MS (M+H): 364.

Example 11: 2,2-dimethyl propyl 5-(3-hydroxy-3-methylbut-1-yn-1-yl)-2-oxo-1-phenyl-1,2-dihydropyridine-3-carboxylate The compound (100 mg) produced in Example 10 was dissolved in acetonitrile (10 mL), and 2-methyl-3-butyn-2-ol (51 mg), tris(tert-butyl)phosphine (1.0 mL), tetrakis(triphenyl phosphine)palladium (0) (32 mg), copper iodide (I) (3.0 mg) and triethylamine (0.2 mL) were added thereto and stirred at 70° C. for 16 hours. The reaction solution was placed into ice water, followed by extraction with ethyl acetate. The organic layer was dried over sodium sulfate, filtered, and then concentrated under reduced pressure. The resulting residue was purified by silica gel column chromatography (hexane:ethyl acetate=100:0→30:70) to obtain the title compound (55 mg) having the following physical property values.
$^1$H-NMR (CDCl$_3$): δ 1.02, 1.58, 4.01, 7.26-7.38, 7.44-7.49, 7.71, 8.14.

Example 12

5-(3-hydroxy-3-methylbut-1-yn-1-yl)-2-oxo-1-phenyl-1,2-dihydropyridine-3-carboxylic acid The compound (50 mg) produced in Example 11 was dissolved in a mixed solvent of methanol/water (4:1, 3.5 mL), and lithium hydroxide monohydrate (4.0 mg) was added thereto. The mixture was stirred at room temperature for 16 hours. To the reaction solution, 1 N hydrochloric acid was added. The organic layer was extracted with dichloromethane, dried over magnesium sulfate, filtered, and then concentrated under reduced pressure to obtain the title compound (32 mg) having the following physical property values.
$^1$H-NMR (CDCl$_3$): δ 1.59, 7.38-7.41, 7.54-7.59, 7.83, 8.60, 13.74.

Example 13

N-{5-[(6,7-dimethoxy-4-quinolinyl)oxy]-2-pyridinyl}-5-(3-hydroxy-3-methyl-1-butyne-1-yl)-2-oxo-1-phenyl-1,2-dihydro-3-pyridinecarboxamide trifluoroacetate The compound (25 mg) produced in Example 12 and the compound (25 mg) produced in Example 2 were used and subjected to the procedure having the same purpose as in Example 3 to obtain the title compound (10 mg) having the following physical property values.
(LC-MS/ELSD): (retention time: 0.77 min);
$^1$H-NMR (DMSO-d$_6$): δ 1.47, 4.00, 4.02, 6.88, 7.54, 7.55-7.60, 7.70, 7.96, 8.34, 8.45-8.48, 8.72, 12.31.

Examples 13(1) to 13(2)

A corresponding quinoline derivative in place of the compound produced in Example 2 and the compound produced in Example 12 were used and subjected to the procedure having the same purpose as in Example 3 to obtain compounds of the following Examples.

Example 13(1)

5-(3-hydroxy-3-methyl-1-butyne-1-yl)-N-{5-[(7-methoxy-4-quinolinyl)oxy]-2-pyridinyl}-2-oxo-1-phenyl-1,2-dihydro-3-pyridinecarboxamide (LC-MS/ELSD): (retention time: 0.86 min);
$^1$H-NMR (CDCl$_3$): δ 1.60, 2.00, 3.97, 6.43, 7.23, 7.38-7.44, 7.51-7.59, 7.81, 8.20-8.26, 8.46, 8.61, 8.71, 12.24.

Example 13(2)

5-(3-hydroxy-3-methyl-1-butyne-1-yl)-N-{5-[(6-methoxy-4-quinolinyl)oxy]-2-pyridinyl}-2-oxo-1-phenyl-1,2-dihydro-3-pyridinecarboxamide (LC-MS/ELSD): (retention time: 0.80 min);
$^1$H-NMR (CDCl$_3$): δ 1.61, 2.02, 3.97, 6.54, 7.39-7.43, 7.51-7.59, 7.81, 8.00, 8.26, 8.47, 8.55, 8.71, 12.25.

Example 14: 3-bromo-1-phenyl-5-(trifluoromethyl)-2(1H)-pyridinone 3-bromo-5-(trifluoromethyl)pyridine-2(1H)-one (1.0 g) was used and subjected to the procedure having the same purpose as in Example 10 to obtain the title compound (1.1 g) having the following physical property values.
$^1$H-NMR (CDCl$_3$): δ 7.36-7.39, 7.48-7.53, 7.75-7.77, 7.94.

Example 15: methyl 2-oxo-1-phenyl-5-(trifluoromethyl)-1,2-dihydro-3-pyridine carboxylate The compound (250 mg) produced in Example 14 was dissolved in a mixed solvent of DMF (8.0 mL) and methanol (8.0 mL), the inside of the reaction vessel was subjected to degassing under a nitrogen monoxide atmosphere for 10 minutes. Palladium acetate (II) (36 mg), 1,1'-bis(diphenylphosphino)ferrocene (88 mg) and triethylamine (0.33 mL) were added thereto, and the mixture was stirred under a carbon monoxide atmosphere (100 psi) at 90° C. for 16 hours. The reaction solution was filtered through celite to remove insoluble solids, and then diluted by the addition of dichloromethane. The resulting solution was washed with 10% citric acid aqueous solution, and the resulting organic layer was dried over sodium sulfate, filtered, and then concentrated under reduced pressure to remove the solvent by evaporation to obtain the title compound (140 mg) having the following physical property values. The resulting compound was used for the subsequent reaction without purification.
$^1$H-NMR (CDCl$_3$): δ 3.93, 7.33-7.41, 7.45-7.58, 7.93-7.97, 8.35.

Example 16: 2-oxo-1-phenyl-5-(trifluoromethyl)-1,2-dihydro-3-pyridine carboxylic acid The compound (100 mg) produced in Example 15 was dissolved in THF (2 mL), and sodium trimethylsilanolate (38 mg) was added thereto. The resulting solution was stirred for three hours at room temperature. The reaction solution was filtered. The resulting precipitate was washed with THF to obtain the title compound (45 mg) having the following physical property value. The resulting compound was used for the subsequent reaction without purification.
MS (M+H): 284.

Example 17

N-{5-[(6,7-dimethoxy-4-quinolinyl)oxy]-2-pyridinyl}-2-oxo-1-phenyl-5-(trifluoromethyl)-1,2-dihydro-3-pyridinecarboxamide The compound (60 mg) produced in Example 16 and the compound (62 mg) produced in Example 2 were used and subjected to the procedure having the same purpose as in Example 3 to obtain the title compound (43 mg) having the following physical property values.
(LC-MS/ELSD): (retention time: 0.84 min);
$^1$H-NMR (CDCl$_3$): δ 4.05, 4.06, 6.47, 7.37-7.48, 7.50-7.65, 8.02-8.06, 8.27, 8.47, 8.51, 8.90, 12.08.

Examples 17(1) to 17(2)

A corresponding quinoline derivative in place of the compound produced in Example 2 and the compound produced in Example 16 were used and subjected to the procedure having the same purpose as in Example 3 to obtain compounds of the following Examples.

Example 17(1)

N-{5-[(7-methoxy-4-quinolinyl)oxy]-2-pyridinyl}-2-oxo-1-phenyl-5-(trifluoromethyl)-1,2-dihydro-3-pyridinecarboxamide (LC-MS/ELSD): (retention time: 0.93 min);
$^1$H-NMR (CD$_3$OD): δ 3.97, 6.44, 7.19-7.25, 7.38-7.50, 7.53-7.67, 8.02-8.06, 8.22, 8.26, 8.47, 8.61, 8.90, 12.08.

Example 17(2)

N-{5-[(6-methoxy-4-quinolinyl)oxy]-2-pyridinyl}-2-oxo-1-phenyl-5-(trifluoromethyl)-1,2-dihydro-3-pyridinecarboxamide (LC-MS/ELSD): (retention time: 0.88 min);
$^1$H-NMR (CDCl$_3$): δ 3.96, 6.54, 7.39-7.44, 7.56-7.60, 8.00, 8.02-8.04, 8.27, 8.47, 8.56, 8.89, 12.07.

Example 18: Methyl 5-(1-ethoxy ethenyl)-2-oxo-1-phenyl-1,2-dihydropyridine-3-carboxylate methyl 5-bromo-2-oxo-1-phenyl-1,2-dihydropyridine-3-carboxylate (CAS registration No: 381248-02-8): (100 mg), and tributyl(1-ethoxyvinyl)tin (0.11 mL) was dissolved in 1,4-dioxane (2 mL), and palladium(0)tetrakis(triphenyl phosphine) (8 mg) were added thereto. The resulting mixture was stirred in a sealed tube at 100° C. for 16 hours. The reaction solution was filtered through celite, and water was added to the filtrate, followed by extraction with ethyl acetate. The resulting organic layer was washed with water, and then with a saturated saline solution, dried over sodium sulfate, filtered, and then concentrated under reduced pressure to obtain the title compound (270 mg) having the following physical property value.
MS (M+H): 300.

Example 19: methyl 5-acetyl-2-oxo-1-phenyl-1,2-dihydropyridine-3-carboxylate

The compound (270 mg) produced in Example 18 was dissolved in THF (5 mL), and 2 mol/L hydrochloric acid (2 mL) was added thereto and stirred at room temperature for one hour. The reaction solution was concentrated under reduced pressure. Water was added to the resulting residue, followed by extraction with ethyl acetate. The resulting organic layer was washed with a saturated saline solution, dried over sodium sulfate, and then concentrated under reduced pressure to obtain the title compound (80 mg) having the following physical property value.
MS (M+H): 272.

Example 20: 5-acetyl-2-oxo-1-phenyl-1,2-dihydropyridine-3-carboxylic acid

The compound (80 mg) produced in Example 19 was dissolved in a mixed solvent of THF/water (4:1, 5 mL), and lithium hydroxide monohydrate (62 mg) was added thereto, and the resulting mixture was stirred at room temperature for 16 hours. To the reaction solution, 1 N hydrochloric acid was added. The organic layer was extracted with dichloromethane, dried over magnesium sulfate, filtered, and then concentrated under reduced pressure to obtain the title compound (50 mg) having the following physical property values.
$^1$H-NMR (CDCl$_3$): δ 2.59, 7.39-7.42, 7.58-7.62, 8.47, 9.07.

Example 21

5-acetyl-N-{5-[(6,7-dimethoxy-4-quinolinyl)oxy]-2-pyridinyl}-2-oxo-1-phenyl-1,2-dihydro-3-pyridinecarboxamide The compound (50 mg) produced in Example 20 and the compound (50 mg) produced in Example 2 were used and subjected to the procedure having the same purpose as in Example 3 to obtain the title compound (17.5 mg) having the following physical property values.
(LC-MS/ELSD): (retention time: 0.73 min);
$^1$H-NMR (CDCl$_3$): δ 2.60, 4.05, 6.47, 7.53-7.60, 8.27, 8.46, 8.47, 8.49, 8.52, 9.20, 12.00.

Example 22: ethyl 6-(tert-butoxycarbonyl)-2,5-dioxo-1-phenyl-1,2,5,6,7,8-hexahydro-1,6-naphthyridine-3-carboxylate Tert-butyl 2,4-dioxopiperidine-1-carboxylate (CAS registration No: 845267-78-9) (3.0 g) was dissolved in DMF at room temperature, and tert-butoxypotassium (13 g) and ethyl (2E)-2-cyano-3-ethoxy prop-2-enoate (CAS registration No: 94-05-3) (2.4 g) were added thereto. The resulting mixture was stirred for 21 hours. The reaction solution was diluted with ethyl acetate, and 2 N aqueous solution of hydrochloric acid was added thereto and the mixture solution was stirred. Furthermore, ethyl acetate and water were added, and the organic layer was extracted. The resulting product was washed with a saturated saline solution, dried over anhydrous sodium sulfate, and a solvent was removed by evaporation under reduced pressure to obtain the title compound (3.5 g) having the following physical property values.
$^1$H-NMR (CDCl$_3$): δ 1.19, 1.43, 2.27, 3.62, 4.09, 8.19.

Example 23

6-(tert-butoxycarbonyl)-2,5-dioxo-1-phenyl-1,2,5,6,7,8-hexahydro-1,6-naphthyridine-3-carboxylic acid The compound (66 mg) produced in Example 22 was dissolved in ethanol (1 mL) at room temperature, aniline (36 mg) was added thereto, and the mixture was stirred at 50° C. for 30 minutes. Solids precipitated from the reaction solution were collected by filtration through Kiriyama funnel, and washed with ethanol. The resulting residue was dried under reduced pressure to obtain the title compound (84 mg) having the following physical property values.
$^1$H-NMR (DMSO-d$_6$): δ 1.46, 2.62, 3.82, 7.43, 7.56-7.62, 8.74, 13.33.

Example 24: 2-methyl-2-propanyl 3-({5-[(6,7-dimethoxy-4-quinolinyl)oxy]-2-pyridinyl}carbamoyl)-2,5-dioxo-1-phenyl-1,5,7,8-tetrahydro-1,6-naphthyridine-6(2H)-carboxylate The compound (80 mg) produced in Example 23 and the compound (68 mg) produced in Example 2 were used and subjected to the procedure having the same purpose as in Example 3 to obtain the title compound (46 mg) having the following physical property values.

TLC: Rf 0.40 (hexane:ethyl acetate=1:2);

$^1$H-NMR (CDCl$_3$): δ 1.56, 2.67, 3.96, 4.04, 6.43, 7.24-7.27, 7.41, 7.52-7.62, 8.20, 8.46, 8.48, 9.39, 11.90.

Example 25

N-{5-[(6,7-dimethoxy-4-quinolinyl)oxy]-2-pyridinyl}-2,5-dioxo-1-phenyl-1,2,5,6,7,8-hexahydro-1,6-naphthyridine-3-carboxamide

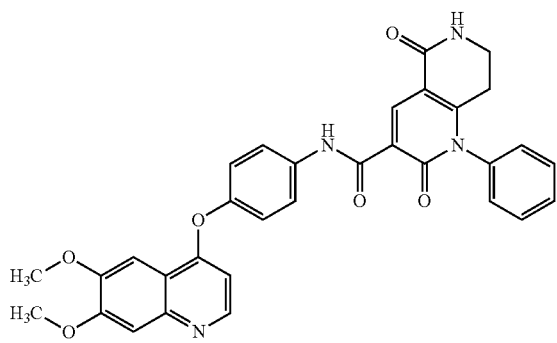 [SMILES: COc1cc2nccc(Oc3ccc(NC(=O)c4cc5c(n(-c6ccccc6)c4=O)CCNC5=O)cc3)c2cc1OC]

The compound (40 mg) produced in Example 24 was dissolved in dichloromethane (3 mL), trifluoroacetic acid (1 mL) was added thereto, and the mixture was stirred at room temperature for 20 minutes. A saturated sodium hydrogen carbonate aqueous solution was added to the reaction solution to neutralize the reaction solution, followed by extraction with dichloromethane. The resulting organic layer was washed with a saturated saline solution, dried over sodium sulfate, filtered, and then concentrated under reduced pressure. The resulting residue was washed with ethyl acetate to obtain the title compound (26 mg) having the following physical property values.

TLC: Rf 0.35 (ethyl acetate, NH silica);

$^1$H-NMR (DMSO-d$_6$): δ 2.25, 2.71, 3.93, 3.94, 6.58, 7.40-7.62, 7.85, 7.96, 8.34, 8.42, 8.50, 8.97, 12.10.

Example 26: Ethyl 3-anilino-3-oxopropanoate

Into a 300-mL three-necked eggplant-type flask, aniline (3.1 g), DMAP (0.61 g), triethylamine (5.1 mL), and dichloromethane (25 mL) were added. A dichloromethane (25 mL) solution of ethyl malonyl chloride (5.0 g) was dropped to the mixture in an ice bath over 20 minutes. The mixture was stirred as it is for 30 minutes. Then, water was added, and dichloromethane was removed by evaporation under reduced pressure. Residues were extracted with ethyl acetate, then washed with 1 N hydrochloric acid and a saturated saline solution sequentially in this order, dried over anhydrous sodium sulfate, and a solvent was removed by evaporation under reduced pressure. The resulting residue was purified by silica gel column chromatography (hexane:ethyl acetate=7:3→1:1) to obtain the title compound (5.8 g) having the following physical property values.

TLC: Rf 0.50 (hexane:ethyl acetate=1:1);

$^1$H-NMR (CDCl$_3$): δ 1.32, 3.47, 4.26, 7.13, 7.35, 7.55, 9.22.

Example 27: ethyl 2-oxo-1-phenyl-1,2-dihydro-1,7-naphthyridine-3-carboxylate

The compound (560 mg) produced in Example 26 was dissolved in toluene (10 mL), 3-bromopyridine-4-carbaldehyde (500 mg), tris(dibenzylideneacetone)dipalladium(0) (120 mg), 4,5-bis(diphenylphosphino)-9,9-dimethylxanthene (160 mg), and cesium carbonate (1800 mg) were added. The mixture was stirred at 150° C. for one hour. Water was added to the reaction solution, followed by extraction with ethyl acetate. The organic layer was dried over sodium sulfate, filtered, and concentrated under reduced pressure. The resulting residue was purified by silica gel chromatography (ethyl acetate) to obtain the title compound (250 mg) having the following physical property values.

TLC: Rf 0.23 (hexane:ethyl acetate=1:1);

$^1$H-NMR (CDCl$_3$): δ 1.41, 4.43, 7.29-7.33, 7.52-7.65, 8.13, 8.41, 8.47.

Example 28

N-{5-[(6,7-dimethoxy-4-quinolinyl)oxy]-2-pyridinyl}-2-oxo-1-phenyl-1,2-dihydro-1,7-naphthyridine-3-carboxamide

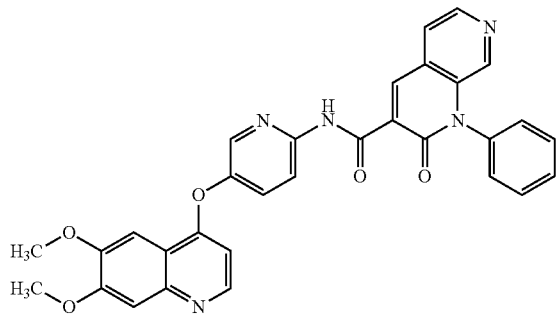 [SMILES: COc1cc2nccc(Oc3ccc(NC(=O)c4cc5ccncc5n(-c5ccccc5)c4=O)nc3)c2cc1OC]

A compound (50 mg) produced by subjecting the compound produced in Example 27 to the procedure having the same purpose as in Example 12, and the compound (56 mg) produced in Example 2 were used and subjected to the procedure having the same purpose as in Example 3 to obtain the title compound (84 mg) having the following physical property values.

TLC: Rf 0.75 (dichloromethane:methanol=9:1);

$^1$H-NMR (DMSO-d$_6$): δ 3.98, 3.99, 6.61, 7.45, 7.57, 7.59-7.79, 7.95, 8.03, 8.16, 8.44, 8.50, 8.54, 8.61, 9.26, 12.34.

Example 29: 7-benzyl-5,6,7,8-tetrahydro-1,7-naphthyridine-2(1H)-one

Ethanol (20 mL) and benzyl bromide (0.8 mL) were added to 1,7-naphthyridine-2(1H)-one (CAS registration No: 54920-82-0) (900 mg), and the mixture was heated and stirred at 80° C. for 18 hours. The mixture was cooled to 0° C., and then sodium borohydride (1100 mg) was added to the mixture. The mixture was stirred at 0° C. for 10 minutes, then hydrochloric acid was added thereto, and the mixture was stirred for 90 minutes at room temperature, followed by neutralization with sodium hydroxide. Then, ethyl acetate was added to the mixture, and the organic layer was extracted. The organic layer was washed with a saturated saline solution, dried over anhydrous sodium sulfate, and a solvent was removed by evaporation under reduced pressure. Thereafter, the resulting solid was washed with ethyl acetate to obtain the title compound (900 mg) having the following physical property values.

$^1$H-NMR (CD$_3$OD): δ 2.66, 2.80, 3.45, 3.75, 6.40, 7.29-7.44.

Example 30: 5,6,7,8-tetrahydro-1,7-naphthyridine-2(1H)-one trifluoroacetate

The compound (800 mg) produced in Example 29 was dissolved in methanol (10 mL), and trifluoroacetic acid (0.27 mL) and palladium carbon (160 mg) were added to the mixture. The mixture was stirred under a hydrogen gas atmosphere at room temperature for five hours. The reaction solution was filtered through celite, and a solvent was removed by evaporation under reduced pressure to obtain the title compound (800 mg) having the following physical property values.

$^1$H-NMR (CD$_3$OD): δ 2.89, 3.51, 4.21, 6.53, 7.48.

Example 31: tert-butyl 2-oxo-2,5,6,8-tetrahydro-1,7-naphthyridine-7(1H)-carboxylate The compound (800 mg) produced in Example 30 was dissolved in THF (10 mL), and triethylamine (1.3 mL) and di-tert-butyl dicarbonate (0.85 mL) were added thereto, and the mixture was stirred at room temperature for three hours. Water was added to the reaction solution, followed by extraction with ethyl acetate. The organic layer was washed with a saturated saline solution and dried over anhydrous sodium sulfate, and a solvent was removed by evaporation under reduced pressure. Thereafter, the resulting solid was washed with a methyl tert-butyl ether (MTBE) solvent to obtain the title compound (760 mg) having the following physical property values.

(LC-MS/ELSD): (retention time: 0.70 min);
$^1$H-NMR (CD$_3$OD): δ 1.52, 2.61, 3.66, 4.43, 6.42, 7.43.

Example 32: tert-butyl 3-bromo-2-oxo-2,5,6,8-tetrahydro-1,7-naphthyridine-7(1H)-carboxylate The compound (490 mg) produced in Example 31 was dissolved in DMF (5 mL), and N-bromosuccinimide (360 mg) was added thereto. The mixture was stirred at room temperature for two hours. The reaction solution was diluted with ethyl acetate, and water was added thereto. The organic layer was extracted. The organic layer was washed with a saturated saline solution and dried over anhydrous sodium sulfate, and a solvent was removed by evaporation under reduced pressure to obtain the title compound (560 mg) having the following physical property values.

TLC: Rf 0.17 (ethyl acetate:methanol=10:1);
$^1$H-NMR (CD$_3$OD): δ 1.52, 2.61, 3.65, 4.39, 7.83.

Example 33: 7-tert-butyl 3-methyl 2-oxo-1-phenyl-2,5,6,8-tetrahydro-1,7-naphthyridine-3,7(1H)-dicarboxylate The compound (1400 mg) produced in Example 32 was used and subjected to the procedure having the same purpose as in Example 10→Example 14 to obtain the title compound (96 mg) having the following physical property values.

(LC-MS/ELSD): (retention time: 1.01 min);
TLC: Rf 0.54 (hexane:ethyl acetate=1:1).

Example 34: tert-butyl 3-({5-[(6,7-dimethoxy quinoline-4-yl)oxy]pyridine-2-yl}carbamoyl)-2-oxo-1-phenyl-2,5,6,8-tetrahydro-1,7-naphthyridine-7(1H)-carboxylate A compound (30 mg) produced by subjecting the compound produced in Example 33 to the procedure having the same purpose as in Example 12, and the compound (17 mg) produced in Example 2 were used and subjected to the procedure having the same purpose as in Example 3 to obtain the title compound (29 mg) having the following physical property values.

TLC: Rf 0.83 (ethyl acetate:methanol=10:1, NH silica);
(LC-MS/ELSD): (retention time: 0.95 min).

Example 35: N-{5-[(6,7-dimethoxy quinoline-4-yl)oxy]pyridine-2-yl}-2-oxo-1-phenyl-1,2,5,6,7,8-hexahydro-1,7-naphthyridine-3-carboxamide trifluoroacetate The compound (25 mg) produced in Example 34 was dissolved in dichloromethane (1 mL), and trifluoroacetic acid (0.03 mL) was added thereto. The mixture was stirred at room temperature for three hours. The reaction solution was concentrated under reduced pressure to obtain the title compound (28 mg) having the following physical property values.

TLC: Rf 0.56 (dichloromethane:methanol: 28% ammonia water=9:1:0.1);
(LC-MS/ELSD): (retention time: 0.69 min).

Example 36

7-(2-butynoyl)-N-{5-[(6,7-dimethoxy-4-quinolinyl)oxy]-2-pyridinyl}-2-oxo-1-phenyl-1,2,5,6,7,8-hexahydro-1,7-naphthyridine-3-carboxamide

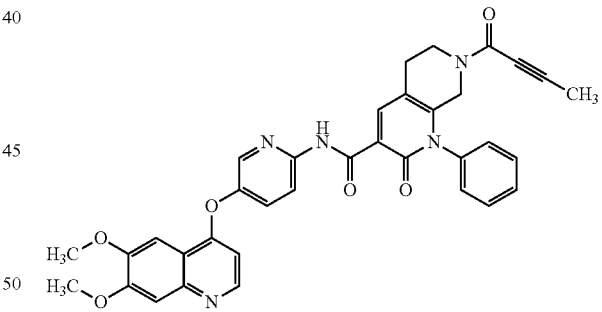

The compound (25 mg) produced in Example 35 and 2-butynoate (3.6 mg) were used and subjected to the procedure having the same purpose as in Example 3 to obtain the title compound (8.0 mg) having the following physical property values.

TLC: Rf 0.42 (ethyl acetate:methanol=10:1);
$^1$H-NMR (CDCl$_3$): δ 1.89 (2.05), 2.82 (2.88), 3.85 (3.99), 4.05, 4.23 (4.37), 6.44, 7.24-7.33, 7.42, 7.52-7.66, 8.23, 8.42-8.54, 12.33 (12.34) (obtained as a mixture of a rotamer).

Example 37: 3-chlorocyclohex-2-ene-1-one

Methanesulfonyl chloride (3.5 mL) and potassium carbonate (19 g) were added to a dichloromethane (230 mL)

solution of cyclohexane-1,3-dione (CAS registration No: 504-02-9) (5.0 g) in an ice bath, and the mixture solution was stirred for four hours. The reaction mixture was washed with water and a saturated saline solution, dried over anhydrous sodium sulfate, and concentrated under reduced pressure to about 150 mL. Benzyltriethylammonium chloride (14 g) and boron trifluoride-ethyl ether complex (1.1 mL) were added to the resulting solution, and the mixture was stirred for 30 minutes. To the reaction mixture, water was poured, followed by extraction with dichloromethane. The resulting organic layer was washed with a saturated saline solution, dried over anhydrous sodium sulfate, and concentrated under reduced pressure. The resulting residue was purified by silica gel chromatography (hexane:ethyl acetate=100:0→80:20) to obtain the title compound (5.2 g) having the following physical property values.

TLC: Rf 0.50 (hexane:ethyl acetate=4:1);
$^1$H-NMR (CDCl$_3$): δ 2.05-2.13, 2.38-2.43, 2.67-2.71, 6.22-6.23.

Example 38:
2-cyano-2-(3-oxocyclohexa-1-en-1-yl)acetamide

A diethylene glycol dimethyl ether (7.0 mL) solution of 2-cyano acetamide (1.2 g) was added to a diethylene glycol dimethyl ether (5.0 mL) solution of sodium hydride (550 mg), and the mixed solution was stirred for 20 minutes. To the mixture solution, a diethylene glycol dimethyl ether (13 mL) solution of the compound (1.2 g) produced in Example 37 was added. The reaction mixture was stirred for 8 hours. The reaction mixture was poured into a hydrochloric acid aqueous solution, followed by extraction with ethyl acetate. The resulting organic layer was washed with a saturated saline solution, dried over anhydrous sodium sulfate, and concentrated under reduced pressure to obtain the title compound (900 mg) having the following physical property value. (LC-MS/ELSD): (retention time: 0.49 min).

Example 39: 3,8-dioxo-2,3,5,6,7,8-hexahydro isoquinoline-4-carbonitrile

N,N-dimethylformamide dimethyl acetal (740 μL) was added to an N,N-dimethylformamide (16 mL) solution of the compound (830 mg) produced in Example 38, and the mixture was stirred for four hours. Water was added to the reaction mixture, followed by extraction with ethyl acetate. The resulting organic layer was washed with a saturated saline solution, dried over anhydrous sodium sulfate, and then concentrated under reduced pressure. The resulting residue was washed with ethyl acetate and collected by filtration to obtain the title compound (350 mg) having the following physical property values.

TLC: Rf 0.52 (ethyl acetate);
$^1$H-NMR (CD$_3$OD): δ 2.10-2.20, 2.62, 3.08, 8.35.

Example 40:
3,8-dioxo-2-phenyl-2,3,5,6,7,8-hexahydro isoquinoline-4-carbonitrile Phenylboronic acid (780 mg), 4 Å molecular sieve (300 mg), copper acetate (II) (580 mg), and pyridine (520 μL) were added to a dichloromethane solution (12 mL) of the compound (300 mg) produced in Example 39. The mixed solution was stirred overnight. A saturated sodium hydrogen carbonate aqueous solution was added to the reaction mixture, and extracted with dichloromethane. The resulting organic layer was washed with a saturated saline solution, dried over anhydrous sodium sulfate, and concentrated under reduced pressure. The resulting residue was purified by silica gel chromatography (hexane:ethyl acetate=50:50→30:70) to obtain the title compound (280 mg) having the following physical property values.

TLC: Rf 0.76 (hexane:ethyl acetate=1:9);
$^1$H-NMR (CDCl$_3$): δ 2.15-2.25, 2.66, 3.14, 7.33-7.39, 7.50-7.56, 8.47.

Example 41:
3,8-dioxo-2-phenyl-2,3,5,6,7,8-hexahydro isoquinoline-4-carboxylic acid Water (0.1 mL) and concentrated sulfuric acid (0.1 mL) were added to the compound (20 mg) produced in Example 40. The reaction mixture was stirred overnight at 100° C. The reaction mixture was poured into a sodium hydroxide aqueous solution and washed with ethyl acetate. A hydrochloric acid aqueous solution was added to the water layer, followed by extraction with ethyl acetate. The resulting organic layer was washed with a saturated saline solution, dried over anhydrous sodium sulfate, concentrated under reduced pressure to obtain the title compound (6.3 mg) having the following physical property values.

TLC: Rf 0.68 (1-butanol:acetic acid:water=4:2:1);
$^1$H-NMR (CDCl$_3$): δ 2.10-2.17, 2.66, 3.69, 7.30-7.44, 7.50-7.68, 8.55.

Example 42

N-{5-[(6,7-dimethoxy-4-quinolinyl)oxy]-2-pyridinyl}-3,8-dioxo-2-phenyl-2,3,5,6,7,8-hexahydro-4-isoquinolinecarboxamide

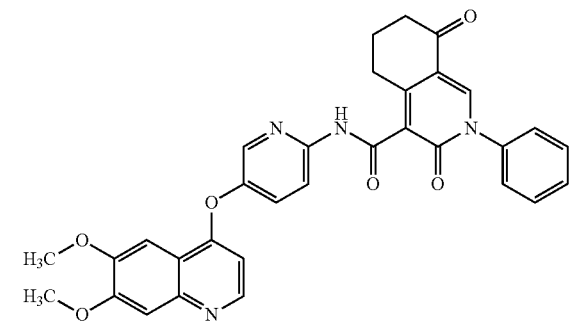 [SMILES: COc1cc2nccc(Oc3ccc(NC(=O)c4c5c(cn(-c6ccccc6)c4=O)C(=O)CCC5)nc3)c2cc1OC]

The compound (6.3 mg) produced in Example 41 and the compound (6.6 mg) produced in Example 2 were used and subjected to the procedure having the same purpose as in Example 3 to obtain the title compound (4.0 mg) having the following physical property values.

TLC: Rf 0.62 (ethyl acetate:methanol=19:1);
$^1$H-NMR (CDCl$_3$): δ 2.10-2.20, 2.67, 3.59, 4.06, 6.45, 7.38-7.45, 7.60-7.52, 8.26, 8.42, 8.51, 8.54, 11.53.

Example 42(1)

N-{4-[(6,7-dimethoxy-4-quinolinyl)oxy]-3-fluorophenyl}-3,8-dioxo-2-phenyl-2,3,5,6,7,8-hexahydro-4-isoquinolinecarboxamide The compound produced in Example 41 and a corresponding quinoline derivative in place of the compound produced in Example 2 were used and subjected to the procedure having the same purpose as in Example 42 to obtain the title compound having the following physical property values.

TLC: Rf 0.30 (ethyl acetate);
$^1$H-NMR (CDCl$_3$): δ 2.05-2.25, 2.67, 3.66, 4.05, 4.06, 6.37-6.47, 7.14-7.24, 7.29-7.36, 7.37-7.44, 7.52-7.66, 7.91, 8.49, 8.52, 11.51.

Example 43: methyl 2-oxo-1-[(1S)-1-phenylethyl]-1,2-dihydropyridine-3-carboxylate Methyl 2-oxopyran-3-carboxylate (CAS registration No: 25991-27-9) (8.4 g) and (1S)-1-phenylethyl amine (7.9 g) were dissolved in DMF (100 mL), and 1-(3-dimethylaminopropyl)-3-ethylcarbodiimide hydrochloride (14 g) and N,N-dimethylpyridine-4-amine (0.67 g) were added to the mixture. The resulting mixture was stirred at room temperature for 16 hours. A saturated sodium hydrogen carbonate aqueous solution was added to the reaction solution, followed by extraction with ethyl acetate. The resulting organic layer was washed with a saturated saline solution, dried over sodium sulfate, then filtered, and concentrated under reduced pressure to obtain the title compound (14 g) having the following physical property values.

TLC: Rf 0.20 (hexane:ethyl acetate=1:1);
$^1$H-NMR (CDCl$_3$): δ 1.73, 3.93, 6.18, 6.53, 7.22-7.41, 8.11.

Example 44: 2-oxo-1-[(1S)-1-phenylethyl]-1,2-dihydropyridine-3-carboxylic acid

The compound (14 g) produced in Example 43 was used and subjected to the procedure having the same purpose as in Example 12 to obtain the title compound (13 mg) having the following physical property values.

TLC: Rf 0.05 (hexane:ethyl acetate=1:1);
$^1$H-NMR (DMSO-d$_6$): δ 1.78, 6.24, 6.74, 7.26-7.46, 8.24, 8.38, 14.56.

Example 45: 5-iodo-2-oxo-1-[(1S)-1-phenylethyl]-1,2-dihydropyridine-3-carboxylic acid The compound (3.0 g) produced in Example 44 was dissolved in dichloromethane (12 mL), and trifluoroacetic acid (12 mL) and N-iodosuccinimide (3.3 g) were added thereto. The mixture was stirred at room temperature for 12 hours. Water was added to the reaction solution, and extracted with dichloromethane. The resulting organic layer was washed with sodium thiosulfate, dried over sodium sulfate, filtered, and then concentrated under reduced pressure. The resulting residue was purified by silica gel chromatography (hexane:ethyl acetate=70:30→50:50) to obtain the title compound (3.5 mg) having the following physical property values.

(LC-MS/ELSD): (retention time: 0.94 min);
$^1$H-NMR (CDCl$_3$): δ 1.80, 6.40, 7.32, 7.37-7.47, 7.62, 8.60, 14.14.

Example 46

N-{5-[(6,7-dimethoxy-4-quinolinyl)oxy]-2-pyridinyl}-5-iodo-2-oxo-1-[(1S)-1-phenylethyl]-1,2-dihydro-3-pyridinecarboxamide The compound (2.0 g) produced in Example 45 and the compound (1.6 mg) produced in Example 2 were used and subjected to the procedure having the same purpose as in Example 3 to obtain the title compound (3.5 g) having the following physical property values.

TLC: Rf 0.67 (ethyl acetate);
$^1$H-NMR (CDCl$_3$): δ 1.80, 4.06, 6.47, 6.50, 7.33-7.46, 7.58, 8.32, 8.47, 8.52, 8.70, 12.55.

Example 47

N-{5-[(6,7-dimethoxy-4-quinolinyl)oxy]-2-pyridinyl}-2-oxo-1-[(1S)-1-phenylethyl]-1,2-dihydro-3-pyridinecarboxamide The compound (100 mg) produced in Example 46 was dissolved in ethanol (4 mL), and 10% palladium-carbon (20 mg) was added thereto. The resulting mixture was stirred under a hydrogen atmosphere at room temperature for three hours. The reaction solution was filtered through celite and the filtrate was concentrated under reduced pressure. The resulting residue was purified by silica gel chromatography (hexane:ethyl acetate=70:30→0:100) to obtain the title compound (30 mg) having the following physical property values.

TLC: Rf 0.42 (ethyl acetate);
$^1$H-NMR (CDCl$_3$): δ 1.81, 4.07, 6.44, 6.48, 6.59, 7.34-7.47, 7.57, 7.58, 8.33, 8.50, 8.52, 8.59, 12.77.

Example 48: Ethyl 3-anilino-3-oxopropanoate

Into a 300-mL three-necked eggplant-type flask, aniline (3.1 g), 4-dimethylaminopyridine (0.61 g), triethylamine (5.1 mL), and dichloromethane (25 mL) were added. A dichloromethane (25 mL) solution of ethyl malonyl chloride (5.0 g) was dropped to the mixture in an ice bath over 20 minutes. The mixture was stirred as it is for 30 minutes. Then, water was added, and dichloromethane was removed by evaporation under reduced pressure. Residues were extracted with ethyl acetate, then washed with 1 N hydrochloric acid and a saturated saline solution sequentially in this order, dried over anhydrous sodium sulfate, and a solvent was removed by evaporation under reduced pressure. The resulting residue was purified by silica gel column chromatography (hexane:ethyl acetate=7:3→1:1) to obtain the title compound (5.8 g) having the following physical property values.

TLC: Rf 0.50 (hexane:ethyl acetate=1:1);
$^1$H-NMR (CDCl$_3$): δ 1.32, 3.47, 4.26, 7.13, 7.35, 7.55, 9.22.

Example 49: 6-methyl-2-oxo-1-phenyl-1,2-dihydro-3-pyridine carboxylic acid

Into a 200-mL eggplant-type flask, the compound (5.8 g) produced in Example 48, (E)-4-methoxy-3-butene-2-one (3.1 g), 20% sodium ethoxide ethanol solution (11.4 g), and methanol (30 mL) were added. The mixture was heated and refluxed for 16 hours, and allowed to cool to room temperature, and a solvent was removed by evaporation under reduced pressure. Then, 2 N sodium hydroxide aqueous solution (30 mL) and methanol (30 mL) were added to the resulting residue and the mixture was stirred at room temperature for 23 hours. Water was added to the reaction solution. The mixture solution was washed with ethyl acetate, and the water layer was made to have pH of 3 to 4 with 5 N hydrochloric acid. Precipitated powder was collected by filtration, and dried to obtain the title compound (3.0 g) having the following physical property values.
TLC: Rf 0.60 (ethyl acetate:methanol=9:1);
$^1$H-NMR (DMSO-d$_6$): δ 2.15, 6.54, 7.24, 7.63, 8.51, 14.0.

Example 50: Methyl 6-methyl-2-oxo-1-phenyl-1,2-dihydro-3-pyridine carboxylate

Into a 200-mL eggplant-type flask, the compound (2.9 g) produced in Example 49, methanol (29 mL), ethyl acetate (29 mL), and trimethylsilyldiazomethane were added. A solvent was removed by evaporation under reduced pressure to obtain the title compound (2.9 g) having the following physical property values.
TLC: Rf 0.34 (ethyl acetate);
$^1$H-NMR (CDCl$_3$): δ 2.04, 3.88, 6.22, 7.18, 7.50, 8.20.

Example 51: Methyl 5-bromo-6-(bromomethyl)-2-oxo-1-phenyl-1,2-dihydro-3-pyridine carboxylate Into a 100-mL eggplant-type flask, the compound (2 g) produced in Example 50, N-bromosuccinimide (3.1 g), benzoyl peroxide (40 mg), and carbon tetrachloride (36 mL) were added. The mixture was heated at 80° C. for six hours. The temperature was returned to room temperature, and precipitates were removed from the reaction solution, and a solvent was removed by evaporation under reduced pressure. The resulting residue was washed with a small amount of ethyl acetate and hexane to obtain the title compound (2.9 g) having the following physical property values.
TLC: Rf 0.29 (hexane:ethyl acetate=1:1);
$^1$H-NMR (CDCl$_3$): δ 3.89, 4.14, 7.29, 7.54, 8.33.

Example 52: Methyl 6-[(bis{[(2-methyl-2-propanyl) oxy]carbonyl}amino)methyl]-5-bromo-2-oxo-1-phenyl-1,2-dihydro-3-pyridine carboxylate Into a 100-mL eggplant-type flask, the compound (2.5 g) produced in Example 51, di-tert-butyl imidodicarbonate (Boc$_2$NH) (1.6 g), potassium carbonate (1.7 g), and DMF (30 mL) were added. The mixture was stirred at room temperature for four hours, and then a saturated aqueous solution ammonium chloride was added thereto, extracted with ethyl acetate, and washed with water and a saturated saline solution sequentially in this order, and dried over anhydrous sodium sulfate, and a solvent was removed by evaporation under reduced pressure. The resulting residue was purified by silica gel column chromatography (hexane: ethyl acetate=7:3→1:1) to obtain the title compound (2.9 g) having the following physical property values.
TLC: Rf 0.40 (hexane:ethyl acetate=1:1);
$^1$H-NMR (CDCl$_3$): δ 1.40, 3.88, 4.67, 7.20, 7.47, 8.34.

Example 53

6-[(bis{[(2-methyl-2-propanyl)oxy]carbonyl}amino) methyl]-5-bromo-2-oxo-1-phenyl-1,2-dihydro-3-pyridine carboxylic acid Into a 100-mL eggplant-type flask, the compound (2.9 g) produced in Example 52, 2 N sodium hydroxide aqueous solution (14 mL), and methanol (14 mL) were added. The mixture was stirred for 30 minutes. To the reaction solution, 1 N hydrochloric acid was added. Precipitated powder was collected by filtration and dried to obtain the title compound (2.3 g) having the following physical property values.

TLC: Rf 0.57 (ethyl acetate);
$^1$H-NMR (CDCl$_3$): δ 1.42, 4.69, 7.26, 7.59, 8.67, 13.77.

Example 54: bis(2-methyl-2-propanyl) {[3-bromo-5-({5-[(6,7-dimethoxy-4-quinolinyl)oxy]-2-pyridinyl}carbamoyl)-6-oxo-1-phenyl-1,6-dihydro-2-pyridinyl]methyl}imidodicarbonate The compound produced in Example 53 (530 mg) and the compound (300 mg) produced in Example 2 were used and subjected to the procedure having the same purpose as in Example 3 to obtain the title compound (770 mg) having the following physical property values.
TLC: Rf 0.54 (ethyl acetate);
$^1$H-NMR (CDCl$_3$): δ 1.43, 4.07, 4.73, 6.51, 7.28, 7.48, 7.50-7.60, 8.23, 8.47, 8.50, 8.78, 12.25.

Example 55

6-(aminomethyl)-N-{5-[(6,7-dimethoxy-4-quinolinyl)oxy]-2-pyridinyl}-2-oxo-1-phenyl-1,2-dihydro-3-pyridinecarboxamide The compound (100 mg) produced in Example 54 was dissolved in ethanol (2 mL), and 10% palladium-carbon (100 mg) and 1 mol/L hydrochloric acid (0.6 mL) were added thereto. The mixture was stirred under a hydrogen atmosphere at 60° C. for three hours. Disappearance of raw material was observed, and then the reaction solution was filtered through celite. The filtrate was concentrated under reduced pressure. The resulting residue was dissolved in methanol (2 mL), 1 mol/L hydrochloric acid-dioxane (0.6 mL) was added to the mixture. The mixture was stirred for further one hour. The reaction solution was concentrated under reduced pressure, and the resulting residue was subjected to preparative purification (silica gel Merck 5744, dichloromethane:methanol:28% ammonia water=15:1:0.1) to obtain the title compound (47 mg) having the following physical property values.
TLC: Rf 0.56 (dichloromethane:methanol:ammonia water=9:1:0.1);
$^1$H-NMR (CDCl$_3$): δ 3.51, 4.05, 6.45, 6.82, 7.25, 7.43, 7.52-7.63, 8.22, 8.47, 8.50, 8.74, 12.36.

Example 56

6-[(2-butynoylamino)methyl]-N-{5-[(6,7-dimethoxy-4-quinolinyl)oxy]-2-pyridinyl}-2-oxo-1-phenyl-1,2-dihydro-3-pyridinecarboxamide The compound produced in Example 55 (45 mg) was used and subjected to the procedure having the same purpose as in Example 36 to obtain the title compound (38 mg) having the following physical property values.
TLC: Rf 0.62 (ethyl acetate:methanol=9:1);
$^1$H-NMR (CDCl$_3$): δ 1.98, 4.05, 4.08, 6.06, 6.45, 6.60, 7.30, 7.42, 7.52-7.65, 8.22, 8.44, 8.49, 8.68, 12.27.

Example 57: N-{5-[(6,7-dimethoxy quinoline-4-yl) oxy]pyridine-2-yl}-5-iodo-2-oxo-1-phenyl-1,2-dihydropyridine-3-carboxamide The compound (1.4 g) produced in Example 3 was used and subjected to the procedure having the same purpose as in Example 45 to obtain the title compound (1.3 g) having the following physical property values.
TLC: Rf 0.50 (hexane:ethyl acetate=4:1);

¹H-NMR (DMSO-d₆): δ 3.90-3.95, 6.54, 7.40, 7.51-7.56, 7.85, 8.36, 8.39, 8.44, 8.48, 8.63, 12.30.

Example 58: 2-methyl-2-propanyl {3-[5-({5-[(6,7-dimethoxy-4-quinolinyl)oxy]-2-pyridinyl}carbamoyl)-6-oxo-1-phenyl-1,6-dihydro-3-pyridinyl]-2-propyn-1-yl}carbamate N-Boc-propargylamine (220 mg), copper iodide (I) (13 mg), tetrakis(triphenyl phosphine) palladium (0) (81 mg), and N,N-diisopropyl ethylamine (360 μL) were added to an N,N-dimethylformamide (5.0 mL) solution of the compound (500 mg) produced in Example 57. The mixture was stirred overnight under an argon atmosphere. Water was added to the reaction mixture, followed by extraction with ethyl acetate. The organic layer was washed with a saturated saline solution, dried over anhydrous sodium sulfate, and then, concentrated under reduced pressure. The resulting residue was purified by silica gel chromatography (hexane:ethyl acetate=40:60→20:80) to obtain the title compound (430 mg) having the following physical property values.

TLC: Rf 0.32 (hexane:ethyl acetate=1:4);
¹H-NMR (CDCl₃): δ 1.47, 4.05, 4.10-4.16, 4.71-4.83, 6.45, 7.37-7.44, 7.50-7.59, 7.81, 8.25, 8.50, 8.70, 12.25.

Example 59: 2-methyl-2-propanyl {3-[5-({5-[(6,7-dimethoxy-4-quinolinyl)oxy]-2-pyridinyl}carbamoyl)-6-oxo-1-phenyl-1,6-dihydro-3-pyridinyl]propyl}carbamate The compound (200 mg) produced in Example 58 was used and subjected to the procedure having the same purpose as in Example 47 to obtain the title compound (200 mg) having the following physical property values.

TLC: Rf 0.11 (hexane:ethyl acetate=1:4);
¹H-NMR (CDCl₃): δ 1.44, 1.68-1.93, 2.57, 3.20, 4.06, 4.54-4.65, 6.49, 7.41-7.60, 8.26, 8.47-8.52, 8.63, 12.58.

Example 60

5-(3-aminopropyl)-N-{5-[(6,7-dimethoxy-4-quinolinyl)oxy]-2-pyridinyl}-2-oxo-1-phenyl-1,2-dihydro-3-pyridinecarboxamide The compound (200 mg) produced in Example 59 was used and subjected to the procedure having the same purpose as in Example 25 to obtain the title compound (150 mg) having the following physical property values.

TLC: Rf 0.11 (ethyl acetate, NH silica);
¹H-NMR (CDCl₃): δ 1.75-1.88, 2.67, 2.77-2.85, 4.05, 6.46, 7.38-7.59, 8.25, 8.46, 8.50, 8.64, 12.57.

Example 61

5-[3-(2-butynoylamino)propyl]-N-{5-[(6,7-dimethoxy-4-quinolinyl)oxy]-2-pyridinyl}-2-oxo-1-phenyl-1,2-dihydro-3-pyridinecarboxamide The compound (89 mg) produced in Example 60 was used and subjected to the procedure having the same purpose as in Example 36 to obtain the title compound (44 mg) having the following physical property values.

TLC: Rf 0.68 (ethyl acetate:methanol=9:1);
¹H-NMR (CDCl₃): δ 1.85-2.0, 2.50-2.65, 3.34-3.42, 4.05, 5.75-5.87, 6.46, 7.42-7.61, 8.25, 8.46, 8.50, 8.62, 12.56.

Example 62: Ethyl 2,5-dioxo-5,6,7,8-tetrahydro-2H-chromene-3-carboxylate 1,3-cyclohexanedione (CAS registration No: 504-02-9) (13 g) was dissolved in N,N-dimethyl formamide (DMF) (200 mL) at room temperature, and tert-butoxy potassium (13 g), ethyl (E)-2-cyano-3-ethoxy-2-propenoate (CAS registration No: 94-05-3) (20 g) were added thereto. The mixture was stirred for 21 hours. The reaction solution was diluted with ethyl acetate, 2 N aqueous solution of hydrochloric acid was added and stirred. Ethyl acetate and waster were further added to the mixture. The organic layer was extracted, and washed with a saturated saline solution, then dried over anhydrous sodium sulfate, and a solvent was removed by evaporation under reduced pressure to obtain the title compound (24 g) having the following physical property values.

TLC: Rf 0.35 (hexane:ethyl acetate=1:1);
¹H-NMR (CDCl₃): δ 1.37, 2.19, 2.61, 2.92, 4.36, 8.63.

Example 63: 2,5-dioxo-1-phenyl-1,2,5,6,7,8-hexahydro-3-quinoline carboxylic acid The compound (10.00 g) produced in Example 62 was dissolved in ethanol (200 mL) at room temperature. To the mixture, aniline (3.94 g) was added. The mixture was stirred for six hours. Solids precipitated from the reaction solution were collected by filtration through Kiriyama funnel, and washed with ethanol. The resulting residue was dried under reduced pressure at 60° C. to obtain the title compound (4.01 g) having the following physical property values.

TLC: Rf 0.37 (dichloromethane:methanol=9:1);
¹H-NMR (CDCl₃): δ 2.11, 2.60, 7.25, 7.63, 9.21.

Example 64

(5E)-5-(hydroxyimino)-4-methyl-2-oxo-1-phenyl-1,2,5,6,7,8-hexahydro-3-quinoline carboxylic acid The compound (140 mg) produced in Example 63 and a pyridine solution (1.0 mL) of hydroxylamine hydrochloride (210 mg) were heated and refluxed for one hour. The resulting solution was cooled to room temperature. The reaction solution was diluted with ethyl acetate and washed with 1 mol/L hydrochloric acid. The resulting organic layer was concentrated to obtain the title compound (150 mg) having the following physical property values.

TLC: Rf 0.42 (dichloromethane:methanol=9:1);
¹H-NMR (DMSO-d₆): δ 1.63-1.81, 2.26-2.36, 2.60, 7.38-7.46, 7.51-7.68, 8.90, 11.30, 14.03.

Example 65

N-{(5E)-5-[(6,7-dimethoxy-4-quinolinyl)oxy]-2-pyridinyl}-5-(hydroxyimino)-2-oxo-1-phenyl-1,2,5,6,7,8-hexahydro-3-quinolinecarboxamide The compound (65 mg) produced in Example 64 and the compound (50 mg) produced in Example 2 were used and subjected to the procedure having the same purpose as in Example 3 to obtain the title compound (59 mg) having the following physical property values.

TLC: 0.15 (ethyl acetate, NH silica);
¹H-NMR (CDCl₃): δ 1.77-1.94, 2.38, 2.77, 4.05, 6.46, 7.20-7.25, 7.43, 7.50-7.65, 7.99-8.07, 8.22, 8.48, 8.52, 9.33, 12.23.

Example 66

N-{5-[(6,7-dimethoxy-4-quinolinyl)oxy]-2-pyridinyl}-2,5-dioxo-1-phenyl-2,5,6,7,8,9-hexahydro-1H-pyrido[3,2-c]azepine-3-carboxamide

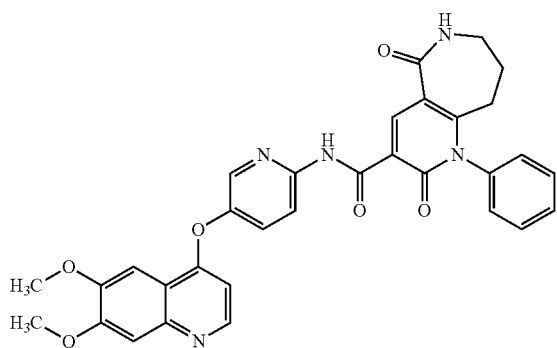 [SMILES: COc1cc2nccc(Oc3ccc(NC(=O)c4cc5c(n(-c6ccccc6)c4=O)CCCNC5=O)nc3)c2cc1OC]

To a dichloromethane solution (1.0 mL) of the compound (30 mg) produced in Example 65, triethylamine (9 μL), dimethyl amino pyridine (0.6 mg) and para-toluenesulfonyl chloride (13 mg) were added and stirred at room temperature for three hours. The reaction solution was diluted with dichloromethane, and washed with water. The organic layer was dried over anhydrous sodium sulfate, and a solvent was removed by evaporation under reduced pressure. To the resulting residue, 50% trifluoroacetic acid/dichloromethane solution (2 mL) was added. The mixture was heated in an oil bath at 70° C. for 16 hours and stirred. The reaction solution was concentrated and the resulting residue was purified by silica gel column chromatography (Chromatorex DNH, ethyl acetate:methanol=1:0→20:1) to obtain the title compound (12 mg) having the following physical property values.

TLC: Rf 0.45 (ethyl acetate:methanol=10:1, DNH silica);
$^1$H-NMR (CDCl$_3$): δ 1.85-2.02, 2.68, 3.23-3.43, 6.23-6.34, 6.44, 7.20-7.25, 7.42, 7.53, 7.55-7.69, 8.21, 8.43-8.52, 9.01, 12.06.

Example 67: diethyl(4-bromo-2-nitrobenzylidene)propanedioate 4-bromo-2-nitrobenzaldehyde (CAS registration No: 5551-12-2) (2.0 mg) was dissolved in acetic anhydride (40 mL), and diethyl malonate (1.4 g) and potassium carbonate (1.8 g) were added thereto. The mixture was stirred at 80° C. for four hours. The reaction solution was allowed to cool to room temperature, and placed into ice water, followed by extraction with dichloromethane. The organic layer was dried over sodium sulfate, filtered, and then concentrated under reduced pressure to yield a crude product (3.2 g) containing the titled compound. The yielded product was used for the subsequent reaction without purification.

Example 68: ethyl 7-bromo-2-oxo-1,2-dihydroquinoline-3-carboxylate

The crude product (2.8 g) produced in Example 67 was dissolved in acetic acid (24 mL). To the mixture, iron powder (4.2 g) was added. The reaction was stirred at 80° C. for four hours. The reaction solution was filtered through celite. A saturated aqueous solution of sodium hydrogen carbonate was added to the filtrate to neutralize the solution, followed by extraction with dichloromethane. The organic layer was dried over sodium sulfate, filtered, and then concentrated under reduced pressure. The resulting residue was washed with tert-butyl methyl ether to obtain the title compound (1.2 g) having the following physical property values.

$^1$H-NMR (CDCl$_3$): δ 1.45, 4.45, 7.34-7.41, 7.48-7.56, 8.50, 10.94.

Example 69: ethyl 7-bromo-2-oxo-1-phenyl-1,2-dihydroquinoline-3-carboxylate

The compound (1.2 g) produced in Example 68, a phenylboronic acid (1.0 g), diacetoxycopper (II) (1.5 g), pyridine (4.0 mL) and 4 Å molecular sieve were added to dichloromethane (200 mL). The mixture was stirred for 64 hours at room temperature under an oxygen atmosphere. The reaction solution was filtered through celite to remove insoluble solids, and then diluted by the addition of dichloromethane (200 mL), and the organic layer was washed with water. The resulting organic layer was dried over sodium sulfate, filtered, and then concentrated under reduced pressure and removed by evaporation. The resulting residue was purified by silica gel column chromatography (hexane:ethyl acetate=70:30) to obtain the title compound (0.88 g) having the following physical property values.

$^1$H-NMR (CDCl$_3$): δ 1.40, 4.41, 6.79-6.82, 7.24-7.25, 7.27-7.29, 7.32-7.38, 7.51-7.66, 8.48.

Example 70: ethyl 7-[(tert-butoxycarbonyl)amino]-2-oxo-1-phenyl-1,2-dihydroquinoline-3-carboxylate The compound produced in Example 69 (800 mg), tert-butylcarbamate (380 mg), cesium carbonate (2.1 g) and 4,5-bis(diphenylphosphino)-9,9-dimethylxanthene (150 mg) were added to 1,4-dioxane (30 mL), and substituted with nitrogen. Then palladium acetate (19 mg) was added to the mixture. The resulting mixture was stirred in a sealed tube at 100° C. for three hours. The reaction solution was filtered through celite and the filtrate was concentrated under reduced pressure. The resulting residue was diluted with ethyl acetate, washed with water, concentrated under reduced pressure, and a solvent was removed by evaporation under reduced pressure to obtain the title compound (880 mg) having the following physical property values.

$^1$H-NMR (CDCl$_3$): δ 1.38, 1.43, 4.39, 6.38, 6.66, 7.22-7.25, 7.45-7.65, 8.50.

Example 71

7-[(tert-butoxycarbonyl)amino]-2-oxo-1-phenyl-1,2-dihydroquinoline-3-carboxylic acid The compound (880 mg) produced in Example 70 was used and subjected to the procedure having the same purpose as in Example 12 to obtain the title compound (650 mg) having the following physical property values.

$^1$H-NMR (DMSO-d$_6$): δ 1.39, 6.96, 7.38-7.45, 7.52-7.72, 8.00-8.05, 8.94, 9.89, 14.24.

Example 72: di-tert-butyl [3-({5-[(6,7-dimethoxy quinoline-4-yl)oxy]pyridine-2-yl}carbamoyl)-2-oxo-1-phenyl-1,2,3,4-tetrahydroquinoline-7-yl]imidodicarbonate The compound (100 mg) produced in Example 71 and the compound (140 mg) produced in Example 2 were used and subjected to the procedure having the same purpose as in Example 3 to obtain the title compound (190 mg) having the following physical property value.

MS (M+H): 660

Example 73

7-amino-N-{5-[(6,7-dimethoxy-4-quinolinyl)oxy]-2-pyridinyl}-2-oxo-1-phenyl-1,2-dihydro-3-quinolinecarboxamide

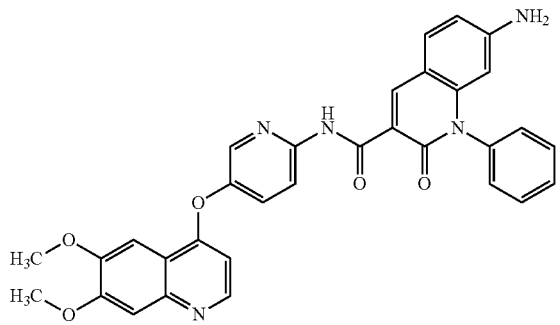 [SMILES: COc1cc2nccc(Oc3ccc(NC(=O)c4cc5ccc(N)cc5n(-c5ccccc5)c4=O)nc3)c2cc1OC]

The compound (190 mg) produced in Example 72 was used and subjected to the procedure having the same purpose as in Example 25 to obtain the title compound (150 mg) having the following physical property values.

(LC-MS/ELSD): (retention time: 0.75 min);
$^1$H-NMR (CDCl$_3$): δ 4.05, 4.26, 5.80, 6.46, 6.63, 7.30-7.42, 7.54, 7.54-7.66, 8.23, 8.48-8.50, 8.95, 12.44.

Examples 73(1) to 73(2)

A corresponding quinoline derivative in place of the compound produced in Example 2 and the compound produced in Example 71 were used and subjected to the procedure having the same purpose as in Example 3→Example 73 to obtain compounds of the following Examples.

Example 73(1)

7-amino-N-{5-[(7-methoxy-4-quinolinyl)oxy]-2-pyridinyl}-2-oxo-1-phenyl-1,2-dihydro-3-quinolinecarboxamide (LC-MS/ELSD): (retention time: 0.78 min);
$^1$H-NMR (CDCl$_3$): δ 4.01, 4.23, 5.80, 6.54, 6.62, 7.53-7.67, 7.54-7.67, 8.22, 8.29, 8.54, 8.69, 8.95, 12.50.

Example 73(2): 7-amino-2-oxo-1-phenyl-N-[5-(4-quinolinyloxy)-2-pyridinyl]-1,2-dihydro-3-quinolinecarboxamide (LC-MS/ELSD): (retention time: 0.76 min);
$^1$H-NMR (CDCl$_3$): δ 4.23, 5.80, 6.55, 6.63, 7.30-7.34, 7.53-7.68, 7.74-7.80, 8.10, 8.23, 8.36, 8.51, 8.69, 8.96, 12.45.

Experiment Example

Biological Experiment Examples are described below. The advantageous effect of the compound of the present invention was verified based on these experiment methods.

Biological Experiment Example 1: Measurement of Axl Inhibitory Activity (In Vitro Test)

Axl enzyme inhibitory activity was measured by using LanthaScreen (registered trademark) system (Invitrogen) based on the attached instruction. The reagents used are shown below.

Reaction buffer solution: a solution containing 50 mmol/L HEPES (pH7.5), 0.01% Brij35, 10 mmol/L MgCl$_2$ and 1 mmol/L EGTA was prepared by using purified water.

Test substance solution: a solution containing a test compound of 5-fold concentration with respect to the final concentration was prepared by 20-fold diluting a DMSO solution of test compound of each concentration with the reaction buffer solution.

Enzyme solution: a solution containing 400 ng/mL Axl enzyme was prepared by using the reaction buffer solution.

Substrate solution: a solution containing 45 μmol/L ATP and 500 nmol/L Fluorescein-Poly GT (Invitrogen) was prepared by using the reaction buffer solution.

Detection solution: a solution containing 20 mM EDTA and 4 nM PY20 (Invitrogen) was prepared by using Dilution B (Invitrogen).

A 10 mmol/L DMSO solution of the test compound was dispensed into a 96-well plate (Nunc), and, furthermore, a 3-fold dilution series was prepared using DMSO. In each well of the 96-well plate for measurement, 5 μL each of the reaction buffer solution containing DMSO was added to a Blank group and a medium group, and 5 μL of the test substance solution was added to the test substance group, respectively. Next, 10 μL/well of the reaction buffer solution was added to the Blank group, and 10 μL/well each of the enzyme solution was added to the medium group and the test compound group, followed by stirring at room temperature for 10 min. After the completion of stirring, 10 μL each of the substrate solution was added into each well, followed by stirring at room temperature with light shielded for one hour. After the completion of reaction, 25 μL each of the detection solution was added to each well, and stood still at room temperature with light shielded for 30 min. After standing sill, fluorescence intensity at 520 nm and 495 nm at the time of irradiation with exciting light of 340 nm was measured by using Analyst GT (Molecular Devices). The phosphorylation of the artificial substrate was quantified by Time-resolved Fluorescence Resonance Energy Transfer (TR-FRET). TR-FRET ratio was calculated by dividing 520 nm fluorescence signal by 495 nm fluorescence signal for each well, and the inhibition rate (%) in the test compound group was calculated based on the following mathematical formula.

$$\text{Inhibition rate (\%)}=[1-(\text{TR-FRET ratio of test compound group}-A)/(B-A)]\times 100 \qquad [\text{Math. 1}]$$

A: average value of TR-FRET ratios of Blank group
B: average value of TR-FRET ratios of medium group Values of 50% inhibition rate (IC50 values) of the test compound were calculated from the inhibition curve based on the inhibition rate of the test compounds in each concentration.

As a result, in the compounds of the present invention, IC50 values of the compounds of, for example, Examples 21, 42, 66, 73, 28 and 36 were 0.0015 μM, 0.0035 μM, 0.0015 μM, 0.004 μM, 0.0013 μM and 0.0015 μM, respectively.

On the other hand, as a comparative compound, the Axl inhibitory activity of the compound 2 (Comparative compound A) in Patent Literature 3 having the following structures, was measured. The IC50 value thereof was higher than 10 μM.

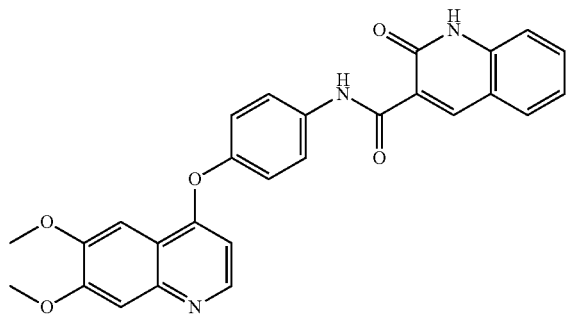 [SMILES: COc1cc2nccc(Oc3ccc(NC(=O)c4cc5ccccc5[nH]c4=O)cc3)c2cc1OC]

Comparative Compound A

Biological Example 2: Measurement of Proliferation Suppression Rate by Using Mouse Pro-B Cell Line (Ba/F3 Axl) Stably Expressing Axl A 0.1 mmol/L DMSO solution of the test compound was dispensed into a 96-well plate, and a 3-fold dilution series was prepared using DMSO. DMSO solutions of test compounds, having various concentrations, were further 500-fold diluted with a RPMI1640 medium (containing 10% HI-FBS, 1% penicillin) and a diluted solution of the test compound having 500-fold concentration with respect to the final concentration was prepared. In each well of the 96-well plate (BD Biosciences) for measurement, 50 μL of a RPMI medium was added to the Blank group, 50 μL of a RPMI medium containing 0.2% DMSO was added to the medium group, and 50 μL of the diluted solution of the test compound was added to the test compound group, respectively. Ba/F3 Axl was diluted with a medium to have a density of $2\times10^5$ cells/mL to prepare a cell suspension. In each well of the 96-well plate for measurement, 50 μL each of the RPMI medium was added to the Blank group, and 50 μL each of the cell suspension to the medium group and the test compound group, respectively, and the groups were stood still at 37° C. at 5% $CO_2$ for 48 hours. After standing still, Relative Light Unit (RLU) was measured by using CELL-TITER-GLO (registered trademark) LUMINESCENT CELL VIABILITY ASSAY (Promega). The measurement was carried out according to the attached instruction. To each well, 100 μL each of light-emitting solution was added. The plate was stirred at room temperature for 3 min and then stool still at room temperature with light shielded for 10 min, and RLU was measured by using Microplate Reader (SpectraMax M5e, Molecular Devices). The average values of RLU of the Blank group and the medium group were respectively calculated, and the proliferation suppression rate of the test compound group was calculated.

Proliferation suppression rate (%)={1−(RLU of test compound group−$A$)/($B$−$A$)}×100   [Math. 2]

A: average value of RLU of Blank group
B: average value of RLU of medium group

A value of 50% inhibition rate (IC50 value) of the test compound was calculated from the inhibition curve based on the inhibition rate in each concentration of the test compound.

As a result, in the compounds of the present invention, IC50 values of the compounds of, for example, Examples 21, 42, 66, 73, 28, and 36 were 0.00096 μM, 0.0042 μM, 0.0057 μM, 0.00076 μM, 0.00099 μM, and 0.00047 μM, respectively.

On the other hand, IC50 value of the comparative compound A was >10 μM.

Biological Example 3: Evaluation of Kinase Selectivity (In Vitro Test)

Similar to Biological Example 1, values of 50% inhibition rate (IC50 value) with respect to the KDR kinase of the test compound was measured. The Axl selective inhibitory activity of the test compound with respect to KDR kinase was calculated based on the above-mentioned ratio of the IC50 values. The calculated values are shown in the following Table 1. As the test compounds, for the compounds of the present invention, the compounds of Examples 21, 42, 66, and 28 were used, and for the comparative compounds, the compound of Example 74 (Comparative compound B) and the compound of Example 92 (Comparative compound C) described in Patent Literature 5, having the following structure, were used.

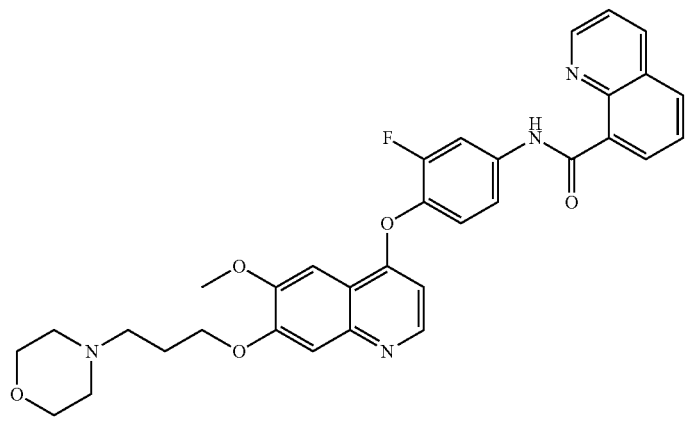

Comparison compound B

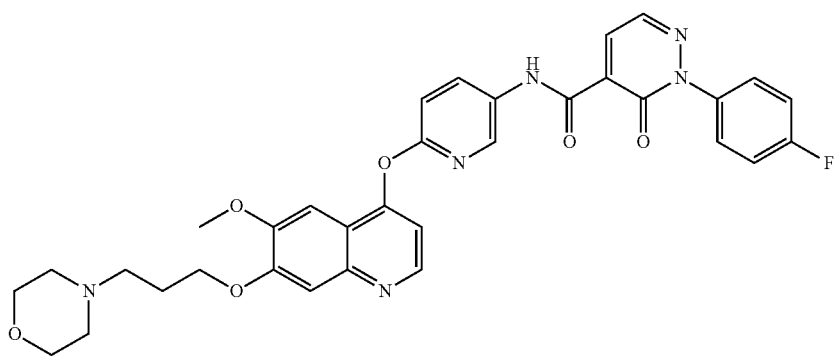

Comparison compound C

TABLE 1

| | KDR [IC50]/Ax1 [IC50] |
|---|---|
| Example 21 | about 149 times |
| Example 42 | about 2857 times |
| Example 66 | about 1401 times |
| Example 28 | about 294 times |
| Comparative compound B | about 0.2 times |
| Comparative compound C | about 28 times |

Results showed that the compound of the present invention had Axl selective inhibition effect on KDR as compared with the comparative compounds. KDR is kinase also referred to as vascular endothelial growth factor receptor 2 (VEGF Receptor 2). It is known that inhibition of KDR may cause a side effect of increasing blood pressure (Hypertension, vol. 39, p. 1095-1100, 2002). Therefore, it was suggested that the compounds of the present invention were excellent compounds capable of avoiding the side effect, which was a problem in comparative compounds, for example, hypertension.

Biological Example 4: Measurement of Inhibitory Activity of Drug-Metabolizing Enzyme (Human CYP2C8 Inhibition Effect)

The reaction was carried out in a 384-well plate. As the positive control substance (CYP2C8: quercetin), a solution, which had been adjusted with DMSO to have 300 times higher concentration than the final concentration (CYP2C8: 22.5 and 225 µmol/L) and been 75-fold diluted with purified water containing 2.7% acetonitrile, was prepared (CYP2C8: 0.3 and 3 µmol/L). The test compounds were prepared to have a concentration of 0.3 and 3 mol/L with DMSO, and then 75-fold diluted with purified water containing 2.7% acetonitrile to be 4 and 40 µmol/L. Then, a reaction mixture solution was prepared by addition of a potassium phosphate buffer (pH 7.4), magnesium chloride (5 mol/L), substrate (CYP2C8: Luciferin-ME, 150 µmol/L), and $E.\ coli$-expressed liver microsome CYP2C8 (Cypex, 30 pmol/L) (the numerical values are final concentrations). The reaction was started by addition of 8 µL of this reaction mixture, 4 µL each of the test compound and the positive control solution which had been prepared as described above, and 4 µL of NADPH production system solution (5.2 mM NADP, 13.2 mM glucose-6-phosphate, 1.6 U/mL glucose-6-phosphate dehydrogenase) and incubation was carried out at 37° C. for 30 min. Thereafter, 16 µL of luciferase solution was added to stop the reaction and to allow luciferin to emit light, and the luminescence intensity of the reaction solution was measured. The inhibition rate is a reduction rate (inhibition rate) of the luminescence intensity when compared with the control in which the reaction was carried out by the addition of DMSO in place of the test compound solution. The inhibition rate was calculated from the following mathematical formula.

$$\text{Inhibition rate (\%)}=100-\{(\text{luminescence intensity of test compound}-\text{background luminescence intensity})/(\text{luminescence intensity of control}-\text{background luminescence intensity})\times 100\} \quad \text{[Math. 3]}$$

The IC50 value was defined to be <1 µM when the inhibition rate at 1 mol/L was not less than 50%; and >10 µM when the inhibition rate at 10 µmol/L was not more than 50%. The range between the above-mentioned range (not more than 50% at 1 µmol/L and not less than 50% at 10 µmol/L) was calculated using the following mathematical formula:

$$IC50=(50-b)/a \quad \text{[Math. 4]}$$

wherein a and b are the slope and intercept of the linear regression line: y=ax+b that passes through the two points: the concentration and the inhibition rate at 1 µmol/L and the concentration and the inhibition rate at 10 µmol/L.

The IC50 value of the compound of the present invention was measured using the measurement method described above.

As a result, the IC50 values of CYP2C8 were >10 µM in the compounds of, for example, Examples 21 and 42 in the present invention. Therefore, it was shown that the compound of the present invention had less CYP inhibition effect.

Formulation Examples

Formulation Example 1

The components indicated below were mixed by a standard method, followed by making the mixture into tablets to obtain 10,000 tablets each containing 10 mg of active ingredient.

| | |
|---|---|
| N-{5-[(6,7-dimethoxy-4-quinolinyl)oxy]-2-pyridinyl}-3,8-dioxo-2-phenyl-2,3,5,6,7,8-hexahydro-4-isoquinolinecarboxamide | 100 g |
| calcium carboxymethyl cellulose (disintegrant) | 20 g |
| magnesium stearate (lubricant) | 10 g |
| microcrystalline cellulose | 870 g |

Formulation Example 2

The components indicated below were mixed by a standard method, filtered through a dust-removing filter, filled into ampoules so that each ampule contains 5 ml, and thermally sterilized in an autoclave to obtain 10,000 ampoules each containing 20 mg active ingredient.

| | |
|---|---|
| N-{5-[(6,7-dimethoxy-4-quinolinyl)oxy]-2-pyridinyl}-3,8-dioxo-2-phenyl-2,3,5,6,7,8-hexahydro-4-isoquinolinecarboxamide | 200 g |
| mannitol | 20 g |
| distilled water | 50 L |

INDUSTRIAL APPLICABILITY

A compound of the present invention has a strong Axl inhibitory activity, and therefore, is useful for treatment for Axl-related diseases, for example, cancer, kidney diseases, immune system diseases, and circulatory system diseases.

The invention claimed is:

1. A compound represented by general formula (I)

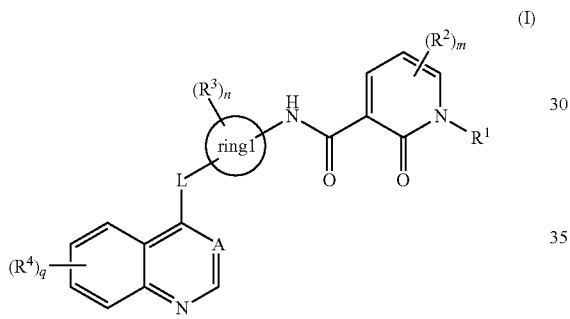

wherein $R^1$ represents (1) a C1-8 alkyl group optionally substituted with one to five $R^{11}$, (2) a C3-7 carbon ring optionally substituted with one to five $R^{12}$, or (3) a 4- to 7-membered heterocycle optionally substituted with one to five $R^{13}$, where when the C1-8 alkyl group represented by $R^1$ is a branched alkyl group, C1-3 alkyl groups branched from the same carbon atom may together form a saturated C3-7 carbon ring;

$R^2$ represents (1) a C1-8 alkyl group optionally substituted with one to five $R^{21}$, (2) a C2-8 alkenyl group optionally substituted with one to five $R^{22}$, (3) a C2-8 alkynyl group optionally substituted with one to five $R^{23}$, (4) a —$OR^{24}$ group, (5) a C3-7 carbon ring optionally substituted with one to five $R^{25}$, (6) a 4- to 7-membered heterocycle optionally substituted with one to five $R^{26}$, (7) a halogen atom, (8) a $C(O)R^{27}$ group, or (9) a $C(O)NR^{28}R^{29}$ group, where when m is two or more and $R^2$ is on adjacent carbon atoms and when $R^2$ represents a C1-3 alkyl group optionally substituted with an amino group, or a C2-3 alkenyl group optionally substituted with an amino group, $R^2$ bonded to the adjacent carbon atoms, together with the carbon atoms, may form a 5- to 7-membered cyclic group optionally substituted with one to three $R^{20}$, and when $R^1$ represents a C1-3 alkyl group, together with the atom on the 5- to 7-membered cyclic group formed by the plurality of $R^2$, may further form a 5- to 7-membered cyclic group;

wherein the ring moiety of the follow in structure of the general formula (I):

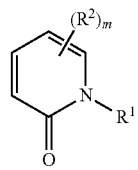

is a ring selected from the group consisting of:

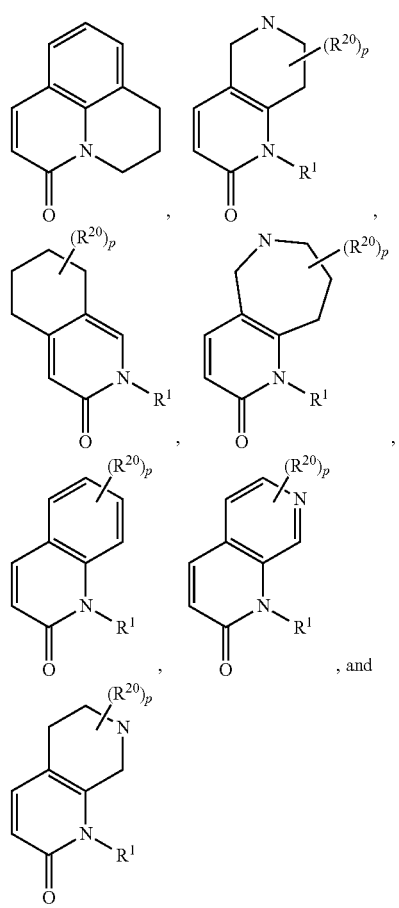

, and wherein p represents an integer of 0 to 3, in which when p is 2 or 3, a plurality of $R^{20}$ may be the same as or different from each other, and each occurrence of —N— appearing in the foregoing rings independently represents —NH— when it is not substituted by $R^{20}$;

$R^3$ represents (1) a C1-4 alkyl group, (2) a halogen atom, (3) a C1-4 haloalkyl group, or (4) —$OR^{31}$ group;

$R^4$ represents (1) a C1-4 alkoxy group, (2) a C1-4 haloalkyl group, (3) an —$OR^{41}$ group, (4) a C1-4 alkyl group, (5) a C2-4 alkenyloxy group, or (6) a C2-4 alkynyloxy group;

$R^{11}$ represents (1) —$OR^{101}$ group, (2) an $SO_2R^{102}$ group, (3) an $NR^{103}R^{104}$ group, or (4) a C3-7 carbon ring optionally substituted with one to three halogen atoms;

$R^{12}$ represents (1) a C1-4 alkyl group optionally substituted with an amino group, (2) a C1-4 haloalkyl group, or (3) a halogen atom;

$R^{13}$ represents (1) a C1-4 alkyl group optionally substituted with an amino group, (2) a C1-4 haloalkyl group, or (3) a halogen atom;

$R^{101}$ represents (1) a hydrogen atom, or (2) a C1-4 alkyl group;

$R^{102}$ represents (1) a hydrogen atom, or (2) a C1-4 alkyl group;

$R^{103}$ and $R^{104}$ each independently represent (1) a hydrogen atom, or (2) a C1-4 alkyl group;

$R^{20}$ represents (1) a C1-4 alkyl group, (2) a halogen atom, (3) a C1-4 haloalkyl group, (4) an oxo group, (5) an —$OR^{201}$ group, (6) a $COOR^{205}$ group, (7) an $NR^{206}R^{207}$ group, or (8) a $COR^{208}$ group, where when two $R^{20}$ represent a C1-3 alkyl group and are on the same carbon atom, the $R^{20}$ together may form a C3-7 saturated carbon ring;

$R^{21}$, $R^{22}$, and $R^{23}$ each independently represents (1) a halogen atom, (2) an $OR^{202}$ group, or (3) an $NR^{203}R^{204}$ group;

$R^{24}$ represents (1) a hydrogen atom, (2) a C1-4 alkyl group, or (3) a 4- to 10-membered heterocycle, $R^{25}$ and $R^{26}$ each independently represent (1) a C1-4 alkyl group, or (2) a halogen atom;

$R^{27}$ represents (1) a hydrogen atom, (2) a C1-4 alkyl group, or (3) a C3-7 carbon ring;

$R^{28}$ and $R^{29}$ each independently represent (1) a hydrogen atom, (2) a C1-4 alkyl group, or (3) a C3-7 carbon ring;

$R^{201}$ represents (1) a hydrogen atom, or (2) a C1-4 alkyl group;

$R^{202}$ represents (1) a hydrogen atom, or (2) a C1-4 alkyl group;

$R^{203}$ and $R^{204}$ each independently represents (1) a hydrogen atom, or (2) a C1-4 alkyl group, (3) a $C(O)R^{210}$ group, or (4) a $COOR^{217}$ group;

$R^{205}$ represents (1) a hydrogen atom, or (2) a C1-4 alkyl group;

$R^{206}$ and $R^{207}$ each independently represent (1) a hydrogen atom, or (2) a C1-4 alkyl group;

$R^{208}$ represents (1) a hydrogen atom, (2) a C1-4 alkyl group, (3) a C2-4 alkenyl group, or (4) a C2-4 alkynyl group;

$R^{210}$ represents (1) a C1-4 alkyl group optionally substituted with $NR^{211}R^{212}$ or a cyano group, (2) a C2-4 alkenyl group optionally substituted with $NR^{213}R^{214}$ or a cyano group, or (3) a C2-4 alkynyl group optionally substituted with $NR^{215}R^{216}$ or a cyano group;

$R^{211}$, $R^{212}$, $R^{213}$, $R^{214}$, $R^{215}$, $R^{216}$ and $R^{217}$ each independently represent (1) a hydrogen atom, or (2) a C1-4 alkyl group;

$R^{31}$ represents (1) a hydrogen atom, (2) a C1-4 alkyl group, or (3) a C1-4 haloalkyl group;

$R^{41}$ represents (1) a hydrogen atom, (2) a C1-8 alkyl group substituted with one to two substituents selected from the group consisting of (a) a 5- to 7-membered cyclic group optionally substituted with one to two substituents selected from the group consisting of (i) a C1-4 alkyl group, (ii) a C1-4 haloalkyl group, and (iii) a halogen atom, (b) $NR^{401}R^{402}$, (c) a hydroxyl group, and (d) an $SO_2R^{403}$ group, (3) a C2-8 alkenyl group substituted with one to two substituents selected from the group consisting of (a) a 5- to 7-membered cyclic group optionally substituted with one to two substituents selected from the group consisting of (i) a C1-4 alkyl group, (ii) a C1-4 haloalkyl group, and (iii) a halogen atom, (b) $NR^{401}R^{402}$, (c) a hydroxyl group, and (d) an $SO_2R^{403}$ group, or (4) a C2-8 alkynyl group substituted with one to two substituents selected from the group consisting of (a) a 5- to 7-membered cyclic group optionally substituted with one to two substituents selected from the group consisting of (i) a C1-4 alkyl group, (ii) a C1-4 haloalkyl group, and (iii) a halogen atom, (b) $NR^{401}R^{402}$, (c) a hydroxyl group, and (d) an $SO_2R^{403}$ group;

$R^{401}$ and $R^{402}$ each independently represent (1) a hydrogen atom, or (2) a C1-4 alkyl group;

$R^{403}$ represents (1) a hydrogen atom, or (2) a C1-4 alkyl group;

A represents (1) CH, or (2) a nitrogen atom;

L represents (1) —O—, (2) —NH—, (3) —C(O)—, (4) —$CR^6R^7$—, (5) —S—, (6) —S(O)—, or (7) —$S(O)_2$—;

$R^6$ and $R^7$ each independently represent (1) a hydrogen atom, (2) a halogen atom, (3) a C1-4 alkyl group, (4) a hydroxyl group, or (5) $NH_2$;

ring1 represents a 5- to 7-membered cyclic group;

$R^{11}$, $R^{12}$, $R^{13}$, $R^{20}$, $R^{21}$, $R^{22}$, $R^{23}$, $R^{25}$, or $R^{26}$, when being a plurality of groups, may be the same as or different from each other;

m represents an integer of 0 to 3;

n represents an integer of 0 to 3;

q represents an integer of 0 to 4;

when m is two or more, a plurality of $R^2$ may be the same as or different from each other;

when n is two or more, a plurality of $R^3$ may be the same as or different from each other;

when q is two or more, a plurality of $R^4$ may be the same as or different from each other, a salt thereof, a solvate thereof, an N-oxide thereof, or a prodrug thereof.

2. The compound according to claim 1, wherein $R^2$ represents (1) a C1-8 alkyl group optionally substituted with one to five $R^{21}$, (2) a C2-8 alkenyl group optionally substituted with one to five $R^{22}$, (3) a C2-8 alkynyl group optionally substituted with one to five $R^{23}$, (4) a halogen atom, or (5) a $C(O)R^{27}$ group.

3. The compound according to claim 1, wherein the ring1 is benzene or pyridine.

4. The compound according to claim 1, wherein L is (1) —O—, (2) —NH—, or (3) —C(O)—.

5. The compound according to claim 1, wherein the compound is
   (1) N-{5-[(6,7-dimethoxy-4-quinolinyl)oxy]-2-pyridinyl}-3,8-dioxo-2-phenyl-2,3,5,6,7,8-hexahydro-4-isoquinolinecarboxamide,
   (2) N-{5-[(6,7-dimethoxy-4-quinolinyl)oxy]-2-pyridinyl}-2,5-dioxo-1-phenyl-2,5,6,7,8,9-hexahydro-1H-pyrido[3,2-c]azepine-3-carboxamide,
   (3) 7-amino-N-{5-[(6,7-dimethoxy-4-quinolinyl)oxy]-2-pyridinyl}-2-oxo-1-phenyl-1,2-dihydro-3-quinolinecarboxamide,
   (4) N-{5-[(6,7-dimethoxy-4-quinolinyl)oxy]-2-pyridinyl}-2-oxo-1-phenyl-1,2-dihydro-1,7-naphthyridine-3-carboxamide,
   (5) 7-(2-butynoyl)-N-{5-[(6,7-dimethoxy-4-quinolinyl)oxy]-2-pyridinyl}-2-oxo-1-phenyl-1,2,5,6,7,8-hexahydro-1,7-naphthyridine-3-carboxamide,
   a salt thereof, a solvate thereof, an N-oxide thereof, or a prodrug thereof.

6. A pharmaceutical composition comprising the compound represented by the general formula (I) as defined in claim 1, a salt thereof, a solvate thereof, an N-oxide thereof, or a prodrug of thereof, and a pharmaceutically acceptable vehicle.

7. The pharmaceutical composition according to claim 6, which is an Axl inhibitor.

8. A method for treating an Axl-related disease, the method comprising administering to a mammal in need thereof an effective amount of a pharmaceutical composition comprising a compound represented by the general formula (I) as defined in claim 1, a salt thereof, a solvate thereof, an N-oxide thereof, or a prodrug thereof, and a pharmaceutically acceptable vehicle, wherein the Axl-related diseases is cancer, kidney diseases, immune system diseases, or circulatory system diseases.

9. The method according to claim 8, wherein the cancer is acute myeloid leukemia, chronic myeloid leukemia, acute lymphatic leukemia, chronic lymphatic leukemia, multiple myeloma, melanoma, breast cancer, pancreatic cancer, glioma, esophageal adenocarcinoma, large intestine cancer, renal cell carcinoma, thyroid cancer, non-small cell lung cancer, prostate cancer, stomach cancer, liver cancer, uveal malignant melanoma, ovarian cancer, endometrial cancer, lymphoma, head and neck cancer, or sarcoma.

10. A method of suppressing metastasis of cancer cells in a cancer patient, comprising administering to the cancer patient an effective amount of a pharmaceutical composition comprising a compound represented by the general formula (I) as defined in claim 1, a salt thereof, a solvate thereof, an N-oxide thereof, or a prodrug thereof, and a pharmaceutically acceptable vehicle.

11. A method for inhibiting Axl in a subject, comprising administering to the subject a pharmaceutical composition comprising a compound represented by the general formula (I) as defined in claim 1, a salt thereof, a solvate thereof, an N-oxide thereof, or a prodrug thereof, and a pharmaceutically acceptable vehicle.

* * * * *

UNITED STATES PATENT AND TRADEMARK OFFICE
CERTIFICATE OF CORRECTION

PATENT NO. : 10,208,034 B2
APPLICATION NO. : 15/539530
DATED : February 19, 2019
INVENTOR(S) : Takayuki Inukai et al.

It is certified that error appears in the above-identified patent and that said Letters Patent is hereby corrected as shown below:

In the Claims

Column 56, Line 1; In Claim 1, delete "follow in" and insert --following-- therefor Column 56, Line 62; In Claim 1, delete "(1) —$OR^{101}$" and insert --(1) an —$OR^{101}$-- therefor Column 57, Line 18; In Claim 1, delete "an $OR^{202}$" and insert --an —$OR^{202}$-- therefor Column 57, Line 66; In Claim 6, after "prodrug", delete "of"

Signed and Sealed this
Twenty-first Day of May, 2019

Andrei Iancu
*Director of the United States Patent and Trademark Office*